US008779118B2

(12) United States Patent
Allerson et al.

(10) Patent No.: US 8,779,118 B2
(45) Date of Patent: Jul. 15, 2014

(54) BASE MODIFIED BICYCLIC NUCLEOSIDES AND OLIGOMERIC COMPOUNDS PREPARED THEREFROM

(75) Inventors: Charles Allerson, San Diego, CA (US); Balkrishen Bhat, Carlsbad, CA (US); Eric E. Swayze, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 111 days.

(21) Appl. No.: 13/519,287

(22) PCT Filed: Jan. 6, 2011

(86) PCT No.: PCT/US2011/020376
§ 371 (c)(1),
(2), (4) Date: Oct. 5, 2012

(87) PCT Pub. No.: WO2011/085102
PCT Pub. Date: Jul. 14, 2011

(65) Prior Publication Data
US 2013/0041011 A1 Feb. 14, 2013

Related U.S. Application Data

(60) Provisional application No. 61/293,787, filed on Jan. 11, 2010.

(51) Int. Cl.
*C07H 19/00* (2006.01)
*C07H 21/04* (2006.01)
*C12Q 1/68* (2006.01)

(52) U.S. Cl.
USPC ............... 536/28.54; 536/23.1; 435/6.1

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lableu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |

(Continued)

FOREIGN PATENT DOCUMENTS

| | | |
|---|---|---|
| WO | WO 94/17093 | 8/1994 |
| WO | WO 99/14226 | 3/1999 |

(Continued)

OTHER PUBLICATIONS

Altschul et al., "Basic Local Alignment Search Tool" J. Mol. Biol. (1990) 215:403-410.
Barany et al., "A New Amino Protecting Group Removable by Reduction. Chemistry of the Dithiasuccinoyl (Dts) Function" J. Am. Chem. Soc. (1977) 99:7363-7365.
Barany et al., "Kinetics and Mechanisms of the Thiolytic Removal of the Dithiasuccinoyl (Dts) Amino Protecting Group" J. Am. Chem. Soc. (1980) 102:3084-3095.
Bass, "Double-stranded RNA as a template for gene silencing" Cell (2000) 101:235-238.
Beaucage et al., "Advances in the Synthesis of Oligonucleotides by the Phosphoramidite Approach" Tetrahedron (1992) 48(12):2223-2311.

(Continued)

*Primary Examiner* — Traviss C McIntosh, III
(74) *Attorney, Agent, or Firm* — Isis Pharmaceuticals, Inc. Patent Dept.

(57) ABSTRACT

Provided herein are novel base modified bicyclic nucleosides, oligomeric compounds prepared therefrom and methods of using the oligomeric compounds. More particularly, novel pyrimidine bicyclic nucleosides are provided wherein each pyrimidine base is substituted at the 5 position with an optionally substituted, aromatic or heteroaromatic ring system comprising from 5 to 7 ring atoms selected from C, N, O and S. In certain embodiments, the oligomeric compounds provided herein hybridize to a portion of a target RNA resulting in loss of normal function of the target RNA.

42 Claims, No Drawings

(56) References Cited

U.S. PATENT DOCUMENTS

| | | |
|---|---|---|
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,426,220 B1 | 7/2002 | Bennett et al. |
| 6,600,032 B1 | 7/2003 | Manoharan et al. |
| 6,770,748 B2 | 8/2004 | Imanishi et al. |
| 6,794,499 B2 | 9/2004 | Wengel et al. |
| 7,399,845 B2 | 7/2008 | Seth et al. |
| 7,427,672 B2 | 9/2008 | Imanishi et al. |
| 8,518,908 B2* | 8/2013 | Hrdlicka et al. ............ 514/49 |
| 2003/0082807 A1 | 5/2003 | Wengel |
| 2003/0087230 A1 | 5/2003 | Wengel |
| 2003/0207841 A1 | 11/2003 | Kaneko et al. |
| 2003/0224377 A1 | 12/2003 | Wengel et al. |
| 2004/0014959 A1 | 1/2004 | Sorensen et al. |
| 2004/0143114 A1 | 7/2004 | Imanishi et al. |
| 2004/0171570 A1 | 9/2004 | Allerson et al. |
| 2004/0192918 A1 | 9/2004 | Imanishi et al. |
| 2004/0219565 A1 | 11/2004 | Kauppinen et al. |
| 2005/0130923 A1 | 6/2005 | Bhat et al. |

FOREIGN PATENT DOCUMENTS

| | | |
|---|---|---|
| WO | WO 02/36743 | 5/2002 |
| WO | WO 2005/121371 | 12/2005 |
| WO | WO 2005/121372 | 12/2005 |
| WO | WO 2006/076102 | 7/2006 |
| WO | WO 2007/134181 | 11/2007 |
| WO | WO 2008/101157 | 8/2008 |
| WO | WO 2008/150729 | 12/2008 |
| WO | WO 2009/006478 | 1/2009 |
| WO | WO 2009/067647 | 5/2009 |

OTHER PUBLICATIONS

Beaucage et al., "The Functionalization of Oligonucleotides Via Phosphoramidite Derivatives" Tetrahedron (1993) 49(10):1925-1963.

Beaucage et al., "The Synthesis of Specific Ribonucleotides and Unrelated Phosphorylated Biomolecules by the Phosphoramidite Method" Tetrahedron (1993) 49(46):10441-10488.

Belikova et al., "Synthesis of Ribonucleosides and Diribonucleoside Phosphates Containing 2-Chloro-Ethylamine and Nitrogen Mustard Residues" Tet. Lett. (1967) 37:3557-3562.

Brazma et al., "Gene expression data analysis" FEBS Letters (2000) 480:17-24.

Carulli et al., "High Throughput Analysis of Differential Gene Expression" J. Cell. Biochem. Suppl. (1998) 30:286-296.

Celis et al., "Gene expression profiling: monitoring transcription and translation products using DNA microarrays and proteomics" FEBS Lett (2000) 480:2-16.

Elbashir, "Duplexes of 21-nucleotide RNAs mediate RNA interference in cultured mammalian cells" Nature (2001) 411:494-498.

Elbashir, "RNA interference is mediated by 21- and 22-nucleotide RNAs" Genes & Devel. (2001) 15:188-200.

Fire et al., "Potent and Specific Genetic Interference by Double-Stranded RNA in *Caenorhabditis elegans*" Nature (1998) 391:806-811.

Fuchs et al., "Identification of Differentially Expressed Genes by Mutually Subtracted RNA Fingerprinting" Anal. Biochem. (2000) 286:91-98.

Gait et al., "Application of chemically synthesized RNA" RNA: Protein Interactions (1998) 1-36.

Gait, "Oligoribonucleotides" Antisense Research and Applications (1993), CRC Press, Boca Raton, pp. 289-301.

Gallo et al., "2'-C-Methyluridine Phosphoramidite: A New Building Block for the Preparation of RNA Analogues Carrying the 2'-Dydroxyl Group" Tetrahedron (2001) 57: 5707-5713.

Going et al., "Molecular Pathology and Future Developments" Eur. J. Cancer (1999) 35:1895-1904.

Gutierrez et al., "5-Heteroaryl-2'-deoxyuridine Analogs. Synthesis and Incorporation into High-Affinity Oligonucleotides" J. Am. Chem. Soc. (1994) 116(13):5540-5544.

Jungblut et al., "Proteomics in human disease: Cancer, heart and infections diseases" Electrophoresis (1999) 20:2100-2110.

Jurecic et al., "Long-distance DD-PCR and cDNA microarrays" Curr. Opin. Microbiol. (2000) 3:316-321.

(56) References Cited

OTHER PUBLICATIONS

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kumar et al., "The first analogues of LNA (locked nucleic acids): phosphorothioate-LNA and 2'-thio-LNA" Bioorg Med Chem Lett. (1998) 8:2219-2222.

Larson et al., "Rapid DNA Fingerprinting of Pathogens by Flow Cytometry" Cytometry (2000) 41:203-208.

Larsson et al., "High-throughput protein expression of cDNA products as a tool in functional genomics" J. Biotech. (2000) 80:143-157.

Madden et al., "Serial analysis of gene expression: from gene discovery to target identification" DDT (2000) 5:415-425.

Miura et al., "Fluorometric determination of total mRNA with oligo(dT) immobilized on microtiter plates" Clin. Chem. (1996) 42:1758-1764.

Montgomery et al., "RNA as a target of double-stranded RNA-mediated genetic interference in *Caenorhabditis elegans*" Proc Natl. Acad. Sci. (1998) 95:15502-7.

Nishikura et al., "A Short Primer on RNAi: RNA-Directed RNA Polymerase Acts as a Key Catalyst" Cell (2001) 107:415-418.

Prashar et al., "READS: A Method for Display of 3'-End Fragment of Restriction Enzyme-Digested cDNAs for Analysis of Differential Gene Expression" Methods Enzymol. (1999) 303:258-272.

Scaringe, "RNA Oligonucleotide Synthesis via 5'-Sily1-2'-Orthoester Chemistry" Methods (2001) 23:206-217.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Sutcliffe et al., "TOGA: An automated parsing technology for analyzing expression of nearly all genes" PNAS (2000) 97:1976-1981.

Tabara et al., "RNAi in *C. elegans*: Soaking in the Genome Sequence" Science (1998) 282:430-431.

Tijsterman et al., "RNA helicase MUT-14-dependent gene silencing triggered in *C. elegans* by short antisense RNAs" Science (2002) 295:694-7.

Timmons et al., "Ingestion of bacterially expressed dsRNAs can produce specific and potent genetic interference in *Caenorhabditis elegans*" Gene (2001) 263:103-112.

Timmons et al., "Specific Interference by Ingested dsRNA" Nature (1998) 395:854.

To, "Identification of Differential Gene Expression by High Throughput Analysis" Comb. Chem. High Throughput Screen (2000) 3:235-241.

Tuschl et al., "Targeted mRNA degradation by double-stranded RNA in vitro" Genes Dev. (1999) 13:3191-7.

Wahlestedt et al., "Potent and nontoxic antisense oligonucleotide containing locked nucleic acids" Proc. Natl. Acad. Sci. USA (2000) 97: 5633-5638.

Zamecnik et al., "Inhibition of Rous sarcoma virus replication and cell transformation by a specific oligodeoxynucleotide" PNAS (1978) 75:280-284.

Zhang et al., "PowerBLAST: A New Network BLAST Application for Interactive or Automated Sequence Analysis and Annotation" Genome Res. (1997) 7:649-656.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

International Search Report for application PCT/US2011/020376 dated Mar. 24, 2011.

* cited by examiner

BASE MODIFIED BICYCLIC NUCLEOSIDES AND OLIGOMERIC COMPOUNDS PREPARED THEREFROM

CROSS REFERENCED TO RELATED APPLICATIONS

This application is a U.S. National Phase filing under 35 U.S.C. §371 claiming priority to International Serial No. PCT/US2011/020376 filed Jan. 6, 2011, which claims priority to U.S. Provisional Application 61/293,787, filed Jan. 11, 2010 each of which is incorporated herein by reference in its entirety.

SEQUENCE LISTING

The present application is being filed along with a Sequence Listing in electronic format. The Sequence Listing is provided as a file entitled CHEM0062USASEQ.TXT, created Jun. 25, 2012, which is 124 Kb in size. The information in the electronic format of the sequence listing is incorporated herein by reference in its entirety.

FIELD OF THE INVENTION

Provided herein are novel base modified bicyclic nucleosides, oligomeric compounds prepared therefrom and methods of using the oligomeric compounds. More particularly, novel pyrimidine bicyclic nucleosides are provided wherein each pyrimidine base is substituted at the 5 position with an optionally substituted aromatic or heteroaromatic ring system. The base modified bicyclic nucleosides are expected to be useful for enhancing one or more properties of the oligomeric compounds they are incorporated into such as for example nuclease resistance. In certain embodiments, the oligomeric compounds provided herein hybridize to a portion of a target RNA resulting in loss of normal function of the target RNA.

BACKGROUND OF THE INVENTION

Targeting disease-causing gene sequences was first suggested more than thirty years ago (Belikova et al., Tet. Lett., 1967, 37, 3557-3562), and antisense activity was demonstrated in cell culture more than a decade later (Zamecnik et al., Proc. Natl. Acad. Sci. U.S.A., 1978, 75, 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense technology is an effective means for reducing the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, pharmacokinetics or affinity for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy. One such group of chemical modifications includes bicyclic nucleosides wherein the furanose portion of the nucleoside includes a bridge connecting two atoms on the furanose ring thereby forming a bicyclic ring system. Such bicyclic nucleosides have various names including BNA's and LNA's for bicyclic nucleic acids or locked nucleic acids respectively.

Various bicyclic nucleosides have been prepared and reported in the patent literature as well as in scientific literature, see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8(16), 2219-2222; Wengel et al., PCT International Application number PCT/DK98/00393 (published as WO 99/14226 on Mar. 25, 1999), filed Sep. 14, 1998; Singh et al., J. Org. Chem., 1998, 63, 10035-10039, the text of each is incorporated by reference herein, in their entirety. Examples of issued US patents and published applications include for example: U.S. Pat. Nos. 6,770,748, 6,268,490 and 6,794,499 and published U.S. applications 20040219565, 20040014959, 20030207841, 20040192918, 20030224377, 20040143114, 20030087230 and 20030082807, the text of each is incorporated by reference herein, in their entirety.

The synthesis of 5-heteroaryl-2'-deoxyuridine analogs along with their incorporation into oligomeric compounds and the Tm evaluations have been reported (see for example: Nielsen, P. Chem Bio Chem 2007, 8, 2106-2116; and Froehler, B. C. J. Am. Chem. Soc. 1994, 116, 5540-5544).

There remains a long-felt need for agents that specifically regulate gene expression via antisense mechanisms. Disclosed herein are bicyclic nucleosides having a modified pyrimidine base and antisense compounds prepared therefrom that are expected to be useful for modulating gene expression pathways, including those relying on mechanisms of action such as RNaseH, RNAi and dsRNA enzymes, as well as other antisense mechanisms based on target degradation or target occupancy. One having skill in the art, once armed with this

BRIEF SUMMARY OF THE INVENTION

Provided herein are novel base modified bicyclic nucleosides, oligomeric compounds prepared therefrom and methods of using the oligomeric compounds. More particularly, novel pyrimidine bicyclic nucleosides are provided wherein each pyrimidine base is substituted at the 5 position with an optionally substituted aromatic or heteroaromatic ring system. The base modified bicyclic nucleosides are expected to be useful for enhancing one or more properties of the oligomeric compounds they are incorporated into such as for example nuclease resistance. In certain embodiments, the oligomeric compounds provided herein hybridize to a portion of a target RNA resulting in loss of normal function of the target RNA. The oligomeric compounds are also expected to be useful as primers and probes in diagnostic applications.

The variables are defined individually in further detail herein. It is to be understood that the base modified bicyclic nucleosides, oligomeric compounds prepared therefrom and methods of using the oligomeric compounds provided here include all combinations of the embodiments disclosed and variables defined herein.

In certain embodiments, bicyclic nucleosides are provided herein having Formula I:

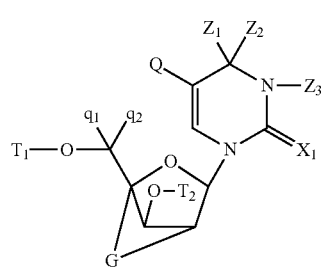

wherein:
one of $T_1$ and $T_2$ is H or a hydroxyl protecting group and the other of $T_1$ and $T_2$ is H, a hydroxyl protecting group or a reactive phosphorus group;

$q_1$ and $q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

$Z_1$ is $NH_2$ or NHPg and $Z_2$ together with $Z_3$ comprise a bond wherein Pg is a protecting group;

or $Z_1$ and $Z_2$ together are =$X_2$ and $Z_3$ is H;

Q is an aryl, substituted aryl, heteroaryl or substituted heteroaryl ring system comprising from 5 to 7 ring atoms independently selected from C, N, O and S;

G is a diradical moiety selected from one or more linked groups, wherein each group is independently selected from —C($R_1R_2$)—, —C($R_1$)=C($R_2$)—, —C($R_1$)=N—, —C[=C($R_1R_2$)]—, —C(=O)—, —N($R_1$)—, —N($R_1$)—C(=$X_3$)—, —O—, —S—, —S(=O)— or —S(=O)$_2$— and wherein G forms a 5 or 6 membered ring with the furanose ring of the nucleoside;

$X_1$, $X_2$ and $X_3$ are each, independently, O or S;

$R_1$ and $R_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

each substituted group comprises one or more optionally protected substituent groups independently selected from halogen, $OJ_1$, $N(J_1)(J_2)$, =$NJ_1$, $SJ_1$, $N_3$, CN, OC(=L)$J_1$, OC(=L)N($J_1$)($J_2$) and C(=L)N($J_1$)($J_2$);

L is O, S or $NJ_3$; and each $J_1$, $J_2$ and $J_3$ is, independently, H, $C_1$-$C_6$ alkyl or $C_1$-$C_6$ substituted alkyl.

In certain embodiments, $q_1$ and $q_2$ are each, independently, H, halogen, $C_1$-$C_6$ alkyl or substituted $C_1$-$C_6$ alkyl. In certain embodiments, $q_1$ and $q_2$ are each H.

In certain embodiments, $Z_1$ is $NH_2$ or NHPg and $Z_2$ together with $Z_3$ comprise a bond. In certain embodiments, $Z_1$ and $Z_2$ together are =$X_2$ and $Z_3$ is H. In certain embodiments, $X_2$ is O.

In certain embodiments, G is —(C($R_1R_2$))$_n$—, —(C($R_1R_2$))$_n$—O—, —(C($R_1R_2$))$_n$—S—, —(C($R_1R_2$))$_n$—(N$R_1$)—, —C(=O)—N($R_1$)—C($R_1R_2$)—, —C($R_1R_2$)—N($R_1$)—C($R_1R_2$)—, —C($R_1R_2$)—N($R_1$)—O— or —C($R_1R_2$)—C(=C($R_1R_2$))—, wherein n is from 1 to 3. In certain embodiments, G is 4'-(CH$_2$)—O-2', 4'-(CH$_2$)$_2$—O-2', 4'-CH(CH$_3$)—O-2', 4'-C(CH$_3$)$_2$—O-2', 4'-CH(CH$_2$OCH$_3$)—O-2', 4'-C(=O)—N(CH$_3$)—CH$_2$-2', 4'-CH$_2$—N(CH$_3$)—CH$_2$-2', 4'-CH$_2$—N(OCH$_3$)-2', 4'-CH$_2$—N(O(CH$_2$)$_2$—OCH$_3$)-2', 4'-CH$_2$—O—N(CH$_3$)—2', 4'-CH$_2$—N(CH$_3$)—O-2', 4'-CH$_2$—CH(CH$_3$)-2' or 4'-CH$_2$—C(=CH$_2$)-2'. In certain embodiments, G is 4'-(CH$_2$)—O-2', 4'-CH(CH$_3$)—O-2', 4'-C(CH$_3$)$_2$—O-2', 4'-CH$_2$—N(OCH$_3$)-2', 4'-CH$_2$—N(O(CH$_2$)$_2$—OCH$_3$)-2', 4'-CH$_2$—O—N(CH$_3$)-2', 4'-CH$_2$—N(CH$_3$)—O-2', 4'-CH$_2$—CH(CH$_3$)-2' or 4'-CH$_2$—C(=CH$_2$)-2'. In certain embodiments, G forms a 5 membered ring with the furanose ring of the nucleoside.

In certain embodiments, Q is aryl or substituted aryl. In certain embodiments, Q is heteroaryl or substituted heteroaryl. In certain embodiments, Q is selected from phenyl, toluenyl, anisolyl, thiazolyl, triazolyl, tetrazolyl, thiophenyl, furanyl, isothiazolyl, oxathiazolyl, oxatriazolyl, dioxazolyl, pyrrolyl, pyrazolyl, imidazolyl, oxazolyl, isooxazolyl, thiadiazolyl, pyridinyl, pyridazinyl, triazinyl, tetrazinyl, thiazinyl, oxathiinyl, azapeninyl, oxepinyl, thiazepinyl, diazepinyl, pyrazinyl and pyrimidinyl. In certain embodiments, Q is triazolyl or tetrazolyl.

In certain embodiments, at least one of $T_1$ and $T_2$ is selected from acetyl, benzyl, t-butyl-dimethylsilyl, t-butyldiphenylsilyl and dimethoxytrityl. In certain embodiments, $T_1$ is 4,4'-dimethoxytrityl. In certain embodiments, $T_2$ is a reactive phosphorus group selected from diisopropylcyanoethoxy phosphoramidite and H-phosphonate. In certain embodiments, $T_1$ is 4,4'-dimethoxytrityl and $T_2$ is diisopropylcyanoethoxy phosphoramidite.

In certain embodiments, bicyclic nucleosides are provided having the configuration of Formula II:

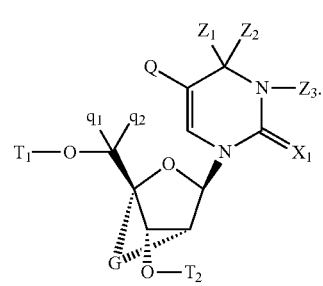

In certain embodiments, oligomeric compounds are provided that each comprise at least one bicyclic nucleoside of Formula III:

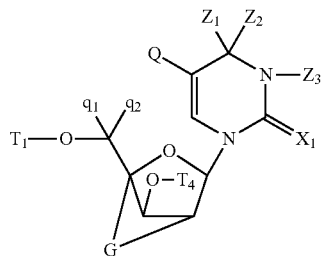

wherein:
wherein independently for each bicyclic nucleoside of Formula III:
one of $T_3$ and $T_4$ is an internucleoside linking group linking the bicyclic nucleoside to the oligomeric compound and the other of $T_3$ and $T_4$ is H, a hydroxyl protecting group, a 5' or 3'-terminal group or an internucleoside linking group linking the bicyclic nucleoside to the oligomeric compound;

$q_1$ and $q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

$Z_1$ is $NH_2$ or NHPg and $Z_2$ together with $Z_3$ comprise a bond wherein Pg is a protecting group;

or $Z_1$ and $Z_2$ together are $=X_2$ and $Z_3$ is H;

Q is an aryl, substituted aryl, heteroaryl or substituted heteroaryl ring system comprising from 5 to 7 ring atoms independently selected from C, N, O and S;

G is a diradical moiety selected from one or more linked groups, wherein each group is independently selected from —C($R_1R_2$)—, —C($R_1$)=C($R_2$)—, —C($R_1$)=N—, —C[=C($R_1R_2$)]—, —C(=O)—, —N($R_1$)—, —N($R_1$)—C(=$X_3$)—, —O—, —S—, —S(=O)— or —S(=O)$_2$— and wherein G forms a 5 or 6 membered ring with the furanose ring of the nucleoside;

$X_1$, $X_2$ and $X_3$ are each, independently, O or S;

$R_1$ and $R_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$; and each $J_1$, $J_2$ and $J_3$ is, independently, H, $C_1$-$C_6$ alkyl or $C_1$-$C_6$ substituted alkyl.

In certain embodiments, $q_1$ and $q_2$ are each independently, H, halogen, $C_1$-$C_6$ alkyl or substituted $C_1$-$C_6$ alkyl for each bicyclic nucleoside of Formula III. In certain embodiments, $q_1$ and $q_2$ are each H for each bicyclic nucleoside of Formula III.

In certain embodiments, $Z_1$ is $NH_2$ or NHPg and $Z_2$ together with $Z_3$ comprise a bond for at least one bicyclic nucleoside of Formula III. In certain embodiments, $Z_1$ and $Z_2$ together are $=X_2$ and $Z_3$ is H for at least one bicyclic nucleoside of Formula III. In certain embodiments, each $X_2$ is O.

In certain embodiments, G is —(C($R_1R_2$))$_n$—, —(C($R_1R_2$))$_n$—O—, —(C($R_1R_2$))$_n$—S—, —(C($R_1R_2$))$_n$—(NR$_1$)—, —C(=O)—N(R$_1$)—C($R_1R_2$)—, —C($R_1R_2$)—O—N(R$_1$)—, —C($R_1R_2$)—N(R$_1$)—O— or —C($R_1R_2$)—C(=C($R_1R_2$))— for each bicyclic nucleoside of Formula III, wherein n is from 1 to 3. In certain embodiments, G is 4'-(CH$_2$)—O-2', 4'-(CH$_2$)$_2$—O-2', 4'-CH(CH$_3$)—O-2', 4'-C(CH$_3$)$_2$—O-2', 4'-C—H(CH$_2$OCH$_3$)—O-2', 4'-C(=O)—N(CH$_3$)—CH$_2$-2', 4'-CH$_2$—N(CH$_3$)—CH$_2$-2', 4'-CH$_2$—N(OCH$_3$)-2', 4'-CH$_2$—N(O(CH$_2$)$_2$—OCH$_3$)-2', 4'-CH$_2$—O—N(CH$_3$)-2', 4'-CH$_2$—N(CH$_3$)—O-2', 4'-CH$_2$—CH(CH$_3$)-2' or 4'-CH$_2$—C(=CH$_2$)-2' for each bicyclic nucleoside of Formula III. In certain embodiments, G is 4'-(CH$_2$)—O-2', 4'-CH(CH$_3$)—O-2', 4'-C(CH$_3$)$_2$—O-2', 4'-CH$_2$—N(OCH$_3$)-2', 4'-CH$_2$—N(O(CH$_2$)$_2$—OCH$_3$)-2', 4'-CH$_2$—O—N(CH$_3$)-2', 4'-CH$_2$—N(CH$_3$)—O-2', 4'-CH$_2$—CH(CH$_3$)-2' or 4'-CH$_2$—C(=CH$_2$)-2' for each bicyclic nucleoside of Formula III. In certain embodiments, G forms a 5 membered ring with the furanose ring of the nucleoside for each bicyclic nucleoside of Formula III.

In certain embodiments, Q is aryl or substituted aryl for each bicyclic nucleoside of Formula III. In certain embodiments, Q is heteroaryl or substituted heteroaryl for each bicyclic nucleoside of Formula III. In certain embodiments, Q is phenyl, toluenyl, anisolyl, thiazolyl, triazolyl, tetrazolyl, thiophenyl, furanyl, isothiazolyl, oxathiazolyl, oxatriazolyl, dioxazolyl, pyrrolyl, pyrazolyl, imidazolyl, oxazolyl, isooxazolyl, thiadiazolyl, pyridinyl, pyridazinyl, triazinyl, tetrazinyl, thiazinyl, oxathiinyl, azapeninyl, oxepinyl, thiazepinyl, diazepinyl, pyrazinyl and pyrimidinyl for each bicyclic nucleoside of Formula III. In certain embodiments, Q is triazolyl or tetrazolyl for each bicyclic nucleoside of Formula III.

In certain embodiments, at least one of $T_3$ and $T_4$ is a 5' or 3'-terminal group.

In certain embodiments, oligomeric compounds are provided that each comprise at least one bicyclic nucleoside of Formula III wherein each bicyclic nucleoside of Formula III further has the configuration of Formula IV:

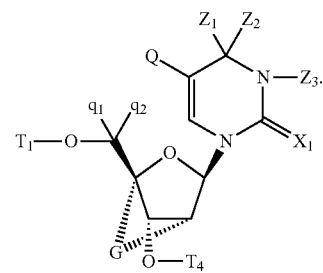

In certain embodiments, oligomeric compounds are provided comprising at least one region of at least two contiguous bicyclic nucleosides located at either the 3' or the 5'-end of the oligomeric compound wherein each bicyclic nucleoside has Formula III or Formula IV.

In certain embodiments, oligomeric compounds are provided comprising gapped oligomeric compounds wherein each of the gapped oligomeric compounds has at least two regions, each region comprising from 1 to about 5 contiguous bicyclic nucleosides having Formula III or Formula IV wherein one of said regions of bicyclic nucleosides is located externally at the 5'-end and the other of said regions is located externally at the 3'-end and wherein the two external regions are separated by an internal region comprising from about 6 to about 14 monomeric subunits independently selected from nucleosides and modified nucleosides.

In certain embodiments, oligomeric compounds are provided comprising from about 8 to about 40 monomers in length.

In certain embodiments, an in vitro method of inhibiting gene expression is provided comprising contacting one or more cells or a tissue with an oligomeric compound of any one of claims 19 to 36.

In certain embodiments, oligomeric compounds are provided for use in an in vivo method of inhibiting gene expression wherein the method comprises contacting one or more cells, a tissue or an animal with an oligomeric compound provided herein.

In certain embodiments, oligomeric compounds are provided herein for use in medical therapy.

In certain embodiments, a method is provided comprising contacting a cell with an oligomeric compound as provided herein wherein said oligomeric compound comprises from about 8 to about 40 monomeric subunits and is complementary to a target RNA. In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function. In certain embodiments, the method further comprises detecting the levels of target RNA.

The variables are defined individually in further detail herein. It is to be understood that the base modified bicyclic nucleosides, oligomeric compound prepared therefrom and the methods of using the oligomeric compounds provided herein include all combinations of the embodiments disclosed and variables defined herein.

DETAILED DESCRIPTION OF THE INVENTION

Provided herein are novel base modified bicyclic nucleosides, oligomeric compounds prepared therefrom and methods of using the oligomeric compounds. More particularly, novel pyrimidine bicyclic nucleosides are provided herein wherein each pyrimidine base is substituted at the 5 position with an optionally substituted, aromatic or heteroaromatic ring system comprising from 5 to 7 ring atoms selected from C, N, O and S. In certain embodiments, the oligomeric compounds provided herein hybridize to a portion of a target RNA resulting in loss of normal function of the target RNA.

In a more general embodiment, base modified bicyclic nucleosides are provided that are incorporated into antisense oligomeric compounds to reduce target RNA, such as messenger RNA, in vitro and in vivo. In one aspect the reduction of target RNA is useful for inhibition of gene expression via numerous pathways. Such pathways include for example the steric blocking of transcription or translation and cleavage of mRNA via single or double stranded oligomeric compounds. The oligomeric compounds provided herein are also expected to be useful as primers and probes in diagnostic applications. In certain embodiments, oligomeric compounds comprising at least one of the base modified bicyclic nucleosides provided herein are expected to be useful as aptamers which are oligomeric compounds capable of binding to aberrant proteins in an in vivo setting.

In certain embodiments, the bicyclic nucleosides (base modified bicyclic nucleosides) provided herein each have Formula I:

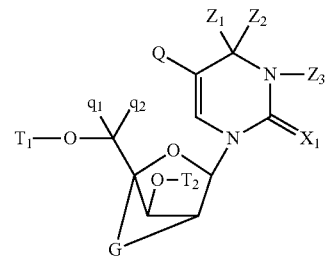

wherein:
one of $T_1$ and $T_2$ is H or a hydroxyl protecting group and the other of $T_1$ and $T_2$ is H, a hydroxyl protecting group or a reactive phosphorus group;

$q_1$ and $q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

$Z_1$ is $NH_2$ or NHPg and $Z_2$ together with $Z_3$ comprise a bond wherein Pg is a protecting group;

or $Z_1$ and $Z_2$ together are $=X_2$ and $Z_3$ is H;

Q is an aryl, substituted aryl, heteroaryl or substituted heteroaryl ring system comprising from 5 to 7 ring atoms independently selected from C, N, O and S;

G is a diradical moiety selected from one or more linked groups, wherein each group is independently selected from —C($R_1R_2$)—, —C($R_1$)═C($R_2$)—, —C($R_1$)═N—, —C[═C($R_1R_2$)]—, —C(═O)—, —N($R_1$)—, —N($R_1$)—C(═$X_3$)—, —O—, —S—, —S(═O)— or —S(═O)$_2$— and wherein G forms a 5 or 6 membered ring with the furanose ring of the nucleoside;

$X_1$, $X_2$ and $X_3$ are each, independently, O or S;

$R_1$ and $R_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

each substituted group comprises one or more optionally protected substituent groups independently selected from halogen, $OJ_1$, $N(J_1)(J_2)$, ═$NJ_1$, $SJ_1$, $N_3$, CN, OC(═L)$J_1$, OC(═L)N($J_1$)($J_2$) and C(═L)N($J_1$)($J_2$);

L is O, S or $NJ_3$; and each $J_1$, $J_2$ and $J_3$ is, independently, H, $C_1$-$C_6$ alkyl or $C_1$-$C_6$ substituted alkyl.

In certain embodiments, each of the bicyclic nucleosides having Formula I further have the configuration of Formula II:

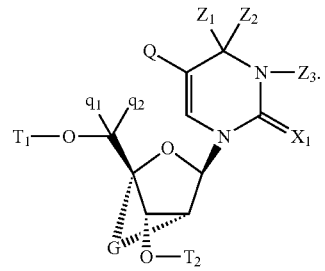

In certain embodiments, oligomeric compounds are provided that each comprise at least one bicyclic nucleoside of Formula III:

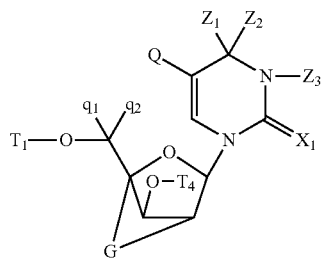

wherein:

wherein independently for each bicyclic nucleoside of Formula III:

one of $T_3$ and $T_4$ is an internucleoside linking group linking the bicyclic nucleoside to the oligomeric compound and the other of $T_3$ and $T_4$ is H, a hydroxyl protecting group, a 5' or 3'-terminal group or an internucleoside linking group linking the bicyclic nucleoside to the oligomeric compound;

$q_1$ and $q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

$Z_1$ is $NH_2$ or NHPg and $Z_2$ together with $Z_3$ comprise a bond wherein Pg is a protecting group;

or $Z_1$ and $Z_2$ together are $=X_2$ and $Z_3$ is H;

Q is an aryl, substituted aryl, heteroaryl or substituted heteroaryl ring system comprising from 5 to 7 ring atoms independently selected from C, N, O and S;

G is a diradical moiety selected from one or more linked groups, wherein each group is independently selected from $-C(R_1R_2)-$, $-C(R_1)=C(R_2)-$, $-C(R_1)=N-$, $-C[=C(R_1R_2)]-$, $-C(=O)-$, $-N(R_1)-$, $-N(R_1)-C(=X_3)-$, $-O-$, $-S-$, $-S(=O)-$ or $-S(=O)_2-$ and wherein G forms a 5 or 6 membered ring with the furanose ring of the nucleoside;

$X_1$, $X_2$ and $X_3$ are each, independently, O or S;

$R_1$ and $R_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$; and each $J_1$, $J_2$ and $J_3$ is, independently, H, $C_1$-$C_6$ alkyl or $C_1$-$C_6$ substituted alkyl.

In certain embodiments, oligomeric compounds are provided that each comprise at least one bicyclic nucleoside of Formula III wherein each bicyclic nucleoside of Formula III further has the configuration of Formula IV:

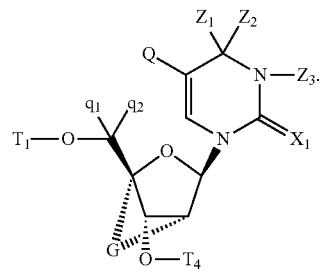

The base modified bicyclic nucleosides provided herein each include a 5 substituted pyrimidine heterocyclic base. The substituent at the 5 position comprises an aromatic ring system (optionally substituted, aryl or heteroaryl) having from 5 to 7 ring atoms selected from C, N, O and S. Such aromatic ring systems include without limitation phenyl, toluenyl, anisolyl and the like (aryl) and thiazolyl, triazolyl, tetrazolyl, thiophenyl, furanyl, isothiazolyl, oxathiazolyl, oxatriazolyl, dioxazolyl, pyrrolyl, pyrazolyl, imidazolyl, oxazolyl, isooxazolyl, thiadiazolyl, pyridinyl, pyridazinyl, triazinyl, tetrazinyl, thiazinyl, oxathiinyl, azapeninyl, oxepinyl, thiazepinyl, diazepinyl, pyrazinyl, pyrimidinyl and the like (heteroaryl).

Incorporation of one or more of the base modified bicyclic nucleosides, as provided herein, into an oligomeric compound is expected to enhance one or more desired properties of the resulting oligomeric compound. Such properties include without limitation stability, nuclease resistance, binding affinity, specificity, absorption, cellular distribution, cellular uptake, charge, pharmacodynamics and pharmacokinetics.

In certain embodiments, the base modified bicyclic nucleosides provided herein are incorporated into oligomeric compounds such that a motif results. The placement of base modified bicyclic nucleosides into oligomeric compounds to provide particular motifs can enhance the desired properties of the resulting oligomeric compounds for activity using a particular mechanism such as RNaseH or RNAi. Such motifs include without limitation, gapped motifs, hemimer motifs, blockmer motifs, uniformly fully modified motifs, positionally modified motifs and alternating motifs. In conjunction with these motifs a wide variety of internucleoside linkages can also be used including but not limited to phosphodiester and phosphorothioate internucleoside linkages which can be incorporated uniformly or in various combinations. The oligomeric compounds can further include at least one 5' or 3' terminal group such as for example a conjugate or reporter group. The positioning of the base modified bicyclic nucleosides provided herein, the use of linkage strategies and 5' or 3' terminal groups can be easily optimized to enhance a desired activity for a selected target.

As used herein the term "motif" refers to the pattern created by the relative positioning of monomer subunits within an oligomeric compound wherein the pattern is determined by comparing the sugar groups. The only determinant for the motif of an oligomeric compound is the differences or lack of differences between the sugar groups. The internucleoside linkage, heterocyclic base and further groups such as terminal groups are not considered when determining the motif of an oligomeric compound. As used herein the term "sugar group" as it applies to motifs includes naturally occurring sugars having a furanose ring, sugars having a modified furanose ring and sugar surrogates wherein the furanose ring has been replaced with another ring system such as for example a morpholino or hexitol ring system or a non-cyclic surrogate. When each sugar group is the same (either modified furanose or surrogate ring system) the motif is termed uniformly fully modified. When two or more types of sugar groups are present the motif is defined by the pattern created from the positioning of monomer subunits having one type of sugar group relative to the positioning of monomer subunits having different types of sugar groups within an oligomeric compound.

Illustrative examples of some different types of sugar groups useful in the preparation of oligomeric compounds having motifs include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose), bicyclic modified sugars (such as the 2'-O—CH$_2$-4' or 2'-O—(CH$_2$)$_2$-4' bridged ribose derived bicyclic sugars) and sugar surrogates (such as for example when the ribose ring has been replaced with a morpholino, a hexitol ring system or an open non-cyclic system). The type of heterocyclic base and internucleoside linkage used at each position is variable and is not a factor in determining the motif. The presence of one or more other groups including but not limited to capping groups, conjugate groups and other 5' or 3'-terminal groups is also not a factor in determining the motif.

Representative U.S. patents that teach the preparation of motifs include without limitation, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

As used herein the term "alternating motif" refers to a an oligomeric compound comprising a contiguous sequence of linked monomer subunits wherein the monomer subunits have two different types of sugar groups that alternate for essentially the entire sequence of the oligomeric compound. Oligomeric compounds having an alternating motif can be described by the formula: 5'-A(-L-B-L-A)$_n$(-L-B)$_{nn}$-3' where A and B are monomer subunits that have different sugar groups, each L is, independently, an internucleoside linking group, n is from about 4 to about 12 and nn is 0 or 1. The heterocyclic base and internucleoside linkage is independently variable at each position. The motif further optionally includes the use of one or more other groups including but not limited to capping groups, conjugate groups and other 5' or 3'-terminal groups. This permits alternating oligomeric compounds from about 9 to about 26 monomer subunits in length. This length range is not meant to be limiting as longer and shorter oligomeric compounds are also amenable to oligomeric compounds provided herein. In certain embodiments, each A or each B comprise base modified bicyclic nucleosides as provided herein.

As used herein the term "uniformly fully modified motif" refers to an oligomeric compound comprising a contiguous sequence of linked monomer subunits that each have the same type of sugar group. The heterocyclic base and internucleoside linkage is independently variable at each position. The motif further optionally includes the use of one or more other groups including but not limited to capping groups, conjugate groups and other 5' or 3'-terminal groups. In certain embodiments, the uniformly fully modified motif includes a contiguous sequence of base modified bicyclic nucleosides. In certain embodiments, one or both of the 5' and 3'-ends of the contiguous sequence of base modified bicyclic nucleosides, comprise 5' or 3'-terminal groups such as one or more unmodified nucleosides.

As used herein the term "hemimer motif" refers to an oligomeric compound comprising a contiguous sequence of monomer subunits that each have the same type of sugar group with a further short contiguous sequence of monomer subunits located at the 5' or the 3' end that have a different type of sugar group. The heterocyclic base and internucleoside linkage is independently variable at each position. The motif further optionally includes the use of one or more other groups including but not limited to capping groups, conjugate groups and other 5' or 3'-terminal groups. In general, a hemimer is an oligomeric compound of uniform sugar groups further comprising a short region (1, 2, 3, 4 or about 5 monomer subunits) having uniform but different sugar groups located on either the 3' or the 5' end of the oligomeric compound.

In certain embodiments, the hemimer motif comprises a contiguous sequence of from about 10 to about 28 monomer subunits having one type of sugar group with from 1 to 5 or from 2 to about 5 monomer subunits having a second type of sugar group located at one of the termini. In certain embodiments, the hemimer is a contiguous sequence of from about 8 to about 20 β-D-2'-deoxyribonucleosides having from 1-12 contiguous base modified bicyclic nucleosides located at one of the termini. In certain embodiments, the hemimer is a contiguous sequence of from about 8 to about 20 β-D-2'-deoxyribonucleosides having from 1-5 contiguous base modified bicyclic nucleosides located at one of the termini. In certain embodiments, the hemimer is a contiguous sequence of from about 12 to about 18 β-D-2'-deoxyribonucleosides having from 1-3 contiguous base modified bicyclic nucleosides located at one of the termini. In certain embodiments, the hemimer is a contiguous sequence of from about 10 to about 14 β-D-2'-deoxyribonucleosides having from 1-3 contiguous base modified bicyclic nucleosides located at one of the termini.

As used herein the terms "blockmer motif" and "blockmer" refer to an oligomeric compound comprising an otherwise contiguous sequence of monomer subunits wherein the sugar groups of each monomer subunit is the same except for an interrupting internal block of contiguous monomer subunits having a different type of sugar group. The heterocyclic base and internucleoside linkage is independently variable at each position of a blockmer. The motif further optionally includes the use of one or more other groups including but not limited to capping groups, conjugate groups and other 5' or 3'-terminal groups. A blockmer overlaps somewhat with a gapmer in the definition but typically only the monomer subunits in the block have non-naturally occurring sugar groups in a blockmer and only the monomer subunits in the external regions have non-naturally occurring sugar groups in a gapmer with the remainder of monomer subunits in the blockmer or gapmer being β-D-2'-deoxyribonucleosides or β-D-ribonucleosides. In certain embodiments, blockmers are provided herein wherein all of the monomer subunits comprise non-naturally occurring sugar groups.

As used herein the term "positionally modified motif" is meant to include an otherwise contiguous sequence of monomer subunits having one type of sugar group that is interrupted with two or more regions of from 1 to about 5 contiguous monomer subunits having another type of sugar group. Each of the two or more regions of from 1 to about 5 contiguous monomer subunits are independently uniformly modified with respect to the type of sugar group. In certain embodiments, each of the two or more regions have the same type of sugar group. In certain embodiments, each of the two or more regions have a different type of sugar group. In certain embodiments, each of the two or more regions, independently, have the same or a different type of sugar group. The heterocyclic base and internucleoside linkage is independently variable at each position of a positionally modified oligomeric compound. The motif further optionally includes the use of one or more other groups including but not limited to capping groups, conjugate groups and other 5' or 3'-terminal groups. In certain embodiments, positionally modified oligomeric compounds are provided comprising a sequence of from 8 to 20 β-D-2'-deoxyribonucleosides that further includes two or three regions of from 2 to about 5 contiguous base modified bicyclic nucleosides each. Positionally modified oligomeric compounds are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is essentially the same. In certain embodiments, each monomer subunit within a particular region has the same sugar group. When the sugar groups of the external regions are the same the gapmer is a symmetric gapmer and when the sugar group used in the 5'-external region is different from the sugar group used in the 3'-external region, the gapmer is an asymmetric gapmer. In certain embodiments, the external regions are small (each independently 1, 2, 3, 4 or about 5 monomer subunits) and the monomer subunits comprise non-naturally occurring sugar groups with the internal region comprising β-D-2'-deoxyribonucleosides. In certain embodiments, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribonucleosides but can comprise non-naturally occurring sugar groups. The heterocyclic base and internucleoside linkage is independently variable at each position of a gapped oligomeric compound. The motif further optionally includes the use of one or more other groups including but not limited to capping groups, conjugate groups and other 5' or 3'-terminal groups.

In certain embodiments, the gapped oligomeric compounds comprise an internal region of β-D-2'-deoxyribonucleosides with one of the external regions comprising base modified bicyclic nucleosides as disclosed herein. In certain embodiments, the gapped oligomeric compounds comprise an internal region of β-D-2'-deoxyribonucleosides with both of the external regions comprising base modified bicyclic nucleosides as provided herein. In certain embodiments, gapped oligomeric compounds are provided herein wherein all of the monomer subunits comprise non-naturally occurring sugar groups.

In certain embodiments, gapped oligomeric compounds are provided comprising one or two base modified bicyclic nucleosides at the 5'-end, two or three base modified bicyclic nucleosides at the 3'-end and an internal region of from 10 to 16 β-D-2'-deoxyribonucleosides. In certain embodiments, gapped oligomeric compounds are provided comprising one base modified bicyclic nucleoside at the 5'-end, two base modified bicyclic nucleosides at the 3'-end and an internal region of from 10 to 16 β-D-2'-deoxyribonucleosides. In certain embodiments, gapped oligomeric compounds are provided comprising one base modified bicyclic nucleosides at the 5'-end, two base modified bicyclic nucleosides at the 3'-end and an internal region of from 10 to 14 β-D-2'-deoxyribonucleosides.

In certain embodiments, gapped oligomeric compounds are provided that are from about 10 to about 21 monomer subunits in length. In certain embodiments, gapped oligomeric compounds are provided that are from about 12 to about 16 monomer subunits in length. In certain embodiments, gapped oligomeric compounds are provided that are from about 12 to about 14 monomer subunits in length.

The terms "substituent" and "substituent group," as used herein, are meant to include groups that are typically added to other groups or parent compounds to enhance desired properties or provide other desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound.

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)—N($R_{bb}$)($R_{cc}$)), thioureido (—N($R_{bb}$)C(S)N($R_{bb}$)($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

The term "alkyl," as used herein, refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

The term "alkenyl," as used herein, refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "acyl," as used herein, refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The term "aminoalkyl" as used herein, refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

The terms "aralkyl" and "arylalkyl," as used herein, refer to an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethyl, pyrimidinylethyl, napthyridinylpropyl and the like. Heteroarylalkyl groups as used herein may optionally include further substituent groups on one or both of the heteroaryl or alkyl portions.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The term "hydrocarbyl" includes radical groups that comprise C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used herein includes all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. Mono or poly cyclic structures can be attached to parent molecules using various strategies such as directly through a ring atom, through a substituent group or through a bifunctional linking moiety.

The term "oxo" refers to the group (=O).

Linking groups or bifunctional linking moieties such as those known in the art are useful for attachment of chemical functional groups, conjugate groups, reporter groups and other groups to selective sites in a parent compound such as for example an oligomeric compound. In general, a bifunctional linking moiety comprises a hydrocarbyl moiety having two functional groups. One of the functional groups is selected to bind to a parent molecule or compound of interest and the other is selected to bind to essentially any selected group such as a chemical functional group or a conjugate group. In some embodiments, the linker comprises a chain structure or a polymer of repeating units such as ethylene glycols or amino acid units. Examples of functional groups that are routinely used in bifunctional linking moieties include without limitation, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include without limitation, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, the oligomeric compounds as provided herein can be modified by covalent attachment of one or more conjugate groups. In general, conjugate groups modify one or more properties of the oligomeric compounds they are attached to. Such oligonucleotide properties include without limitation, pharmacodynamics, pharmacokinetics, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, the oligomeric compounds as provided herein can be modified by covalent attachment of one or more 5' or 3'-terminal groups. The terms "5' or 3'-terminal groups", "5-terminal group" and "3'-terminal group" as used herein are meant to include useful groups known to the art skilled that can be placed on one or both of the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

The term "phosphate moiety" as used herein, refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified (di or tri-phosphates) or modified.

As used herein, the term "phosphorus moiety" refers to a group having the formula:

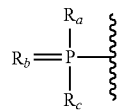

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_c$ is O or S.

Phosphorus moieties included herein can be attached to a monomer, which can be used in the preparation of oligomeric compounds, wherein the monomer may be attached using O, S, $NR_d$ or $CR_eR_f$, wherein $R_d$ includes without limitation H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl, and $R_e$ and $R_f$ each, independently, include without limitation H, halogen, $C_1$-$C_6$ alkyl, substituted $C_1$-$C_6$ alkyl, $C_1$-$C_6$ alkoxy or substituted $C_1$-$C_6$ alkoxy. Such linked phosphorus moieties include without limitation, phosphates, modified phosphates, thiophosphates, modified thiophosphates, phosphonates, modified phosphonates, phosphoramidates and modified phosphoramidates.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.*, 1977, 99, 7363-7365; Barany et al., *J. Am. Chem. Soc.*, 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyl-diphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. No. 4,725,677 and Re. 34,069 (β-cyanoethyl); Beaucage et al., *Tetrahedron*, 1993, 49(10), 1925-1963; Beaucage et al., *Tetrahedron*, 1993, 49(46), 10441-10488; Beaucage et al., *Tetrahedron*, 1992, 48(12), 2223-2311.

In certain embodiments, compounds having reactive phosphorus groups are provided that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite (—O*—P[N[(CH($CH_3$)$_2$]$_2$]O($CH_2$)$_2$CN) and H-phosphonate (—O*—P(=O)(H)OH), wherein the O* is provided from the Markush group for the monomer. A preferred synthetic solid phase synthesis utilizes phosphoramidites ($P^{III}$ chemistry) as reactive phosphites. The intermediate phosphite compounds are subsequently oxidized to the phosphate or thiophosphate ($P^V$ chemistry) using known methods to yield, phosphodiester or phosphorothioate internucleoside linkages. Additional reactive phosphates and phosphites are disclosed in Tetrahedron Report Number 309 (Beaucage and Iyer, *Tetrahedron*, 1992, 48, 2223-2311).

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3(3'-$CH_2$—C(=O)—N(H)-5'), amide-4(3'-$CH_2$—N(H)—C(=O)-5') and methylphosphonate wherein a phosphorus atom is not always present.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most inter-nucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S. Pat. Nos. 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050; 5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include without limitation, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein the phrase "neutral internucleoside linkage" is intended to include internucleoside linkages that are non-ionic. Neutral internucleoside linkages include without limitation, phosphotriesters, methylphosphonates, MMI (3'-$CH_2$—$N(CH_3)$—O-5'), amide-3(3'-$CH_2$—$C(=O)$—$N(H)$-5'), amide-4(3'-$CH_2$—$N(H)$—$C(=O)$-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

The base modified bicyclic nucleosides provided herein can be prepared by any of the applicable techniques of organic synthesis, as, for example, illustrated in the examples below. Many such techniques are well known in the art. However, many of the known techniques are elaborated in *Compendium of Organic Synthetic Methods*, John Wiley & Sons, New York: Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade Jr., 1980; Vol. 5, Leroy G. Wade Jr., 1984; and Vol. 6, Michael B. Smith; as well as March, J., *Advanced Organic Chemistry*, 3rd Edition, John Wiley & Sons, New York, 1985; *Comprehensive Organic Synthesis. Selectivity, Strategy & Efficiency in Modern Organic Chemistry*, in 9 Volumes, Barry M. Trost, Editor-in-Chief, Pergamon Press, New York, 1993; *Advanced Organic Chemistry, Part B: Reactions and Synthesis*, 4th Edition; Carey and Sundberg, Kluwer Academic/Plenum Publishers, New York, 2001; *Advanced Organic Chemistry, Reactions, Mechanisms, and Structure*, 2nd Edition, March, McGraw Hill, 1977; Greene, T. W., and Wutz, P. G. M., *Protecting Groups in Organic Synthesis,* 4th Edition, John Wiley & Sons, New York, 1991; and Larock, R. C., *Comprehensive Organic Transformations,* 2nd Edition, John Wiley & Sons, New York, 1999.

The compounds described herein contain one or more asymmetric centers and thus give rise to enantiomers, diastereomers, and other stereoisomeric forms that may be defined, in terms of absolute stereochemistry, as (R)— or (S)—, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions*, John Wiley & Sons, 1981. When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to limit a particular configuration unless the text so states.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

The term "nucleotide mimetic" as used herein is meant to include monomers that incorporate into oligomeric compounds with sugar and linkage surrogate groups, such as for example peptide nucleic acids (PNA) or morpholinos (linked by —N(H)—C(═O)—O—). In general, the heterocyclic base at each position is maintained for hybridization to a nucleic acid target but the sugar and linkage is replaced with surrogate groups that are expected to function similar to native groups but have one or more enhanced properties.

As used herein the term "nucleoside mimetic" is intended to include those structures used to replace the sugar and the base at one or more positions of an oligomeric compound. Examples of nucleoside mimetics include without limitation replacement of the heterocyclic base moiety with a mimetic thereof such as a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar group with a group such as for example a morpholino, a cyclohexenyl or a bicyclo[3.1.0]hexyl.

As used herein the term "modified nucleoside" is meant to include all manner of modified nucleosides that can be incorporated into an oligomeric compound using oligomer synthesis. The term is intended to include modifications made to a nucleoside such as modified stereochemical configurations, one or more substitutions, and deletion of groups as opposed to the use of surrogate groups which are described elsewhere herein. The term includes nucleosides having a furanose sugar (or 4'-S analog) portion and can include a heterocyclic base or can include an abasic site. One group of representative modified nucleosides includes without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as for example, bicyclic nucleosides wherein the sugar group has a 2'-O—CHR$_a$-4' bridging group, wherein R$_a$ is H, alkyl or substituted alkyl) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as a base and sugar modified nucleosides. These modifications are meant to be illustrative and not exhaustive as other modifications are known in the art and are also envisioned as possible modifications for the modified nucleosides described herein.

As used herein the term "monomer subunit" is meant to include all manner of monomer units that are amenable to oligomer synthesis with one preferred list including monomer subunits such as β-D-ribonucleosides, β-D-2'-deoxyribonucleosides, modified nucleosides, including substituted nucleosides (such as 2', 5' and bis substituted nucleosides), 4'-S-modified nucleosides, (such as 4'-S-ribonucleosides, 4'-S-2'-deoxyribonucleosides and 4'-S-2'-substituted ribonucleosides), bicyclic modified nucleosides (such as bicyclic nucleosides wherein the sugar group has a 2'-O—CHR$_a$-4' bridging group, wherein R$_a$ is H, alkyl or substituted alkyl), other modified nucleosides, nucleoside mimetics, nucleosides having sugar surrogates and the base modified bicyclic nucleosides as provided herein.

The term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and/or increased stability in the presence of nucleases.

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkenyl, sulfamate, methyleneimino, methylenehydrazino, sulfonate, sulfonamide, amide and others having mixed N, O, S and CH$_2$ component parts.

The terms "heterocyclic base moiety" and "nucleobase" as used herein, include unmodified or naturally occurring nucleobases, modified or non-naturally occurring nucleobases as well as synthetic mimetics thereof (such as for example phenoxazines). In general, a heterocyclic base moiety is heterocyclic system that contains one or more atoms or groups of atoms capable of hydrogen bonding to a base of a nucleic acid.

As used herein the terms, "unmodified nucleobase" and "naturally occurring nucleobase" include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4] benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

The heterocyclic base moiety of each of the base modified bicyclic nucleosides can be modified with one or more substituent groups to enhance one or more properties such as affinity for a target strand or affect some other property in an advantageous manner. Modified nucleobases include without limitation, universal bases, hydrophobic bases, promiscuous bases, size-expanded bases, and fluorinated bases as defined herein. Certain of these nucleobases are particularly useful for increasing the binding affinity of the oligomeric compounds as provided herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (*Antisense Research and Applications*, Sanghvi, Y. S., Crooke, S. T. and Lebleu, B., Eds., CRC Press, Boca Raton, 1993, 276-278).

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

In general, the term "oligomeric compound" refers to a contiguous sequence of linked monomer subunits. In general, each linked monomer subunit is directly or indirectly attached to a heterocyclic base moiety but abasic sites are also possible. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having a plurality of non-naturally occurring nucleoside mimetics and or nucleosides having sugar surrogate groups. In certain embodiments, oligomeric compounds comprise a plurality of monomer subunits independently selected from naturally occurring nucleosides, non-naturally occurring nucleosides, modified nucleosides, nucleoside mimetics, and nucleosides having sugar surrogate groups.

When preparing oligomeric compounds having specific motifs as disclosed herein it can be advantageous to mix non-naturally occurring monomer subunits such as the base modified bicyclic nucleosides as provided herein with other non-naturally occurring monomer subunits, naturally occurring monomer subunits (nucleosides) or mixtures thereof. In certain embodiments, oligomeric compounds are provided herein comprising a contiguous sequence of linked monomer subunits wherein at least one monomer subunit is a base modified bicyclic nucleoside as provided herein. In certain embodiments, oligomeric compounds are provided comprising a plurality of base modified bicyclic nucleosides as provided herein.

Oligomeric compounds are routinely prepared linearly but can also be joined or otherwise prepared to be circular and/or can be prepared to include branching. Oligomeric compounds can form double stranded constructs such as for example two strands hybridized to form a double stranded composition. Double stranded compositions can be linked or separate and can include various other groups such as conjugates and/or overhangs on the ends.

Oligomeric compounds provided herein can optionally contain one or more nucleosides wherein the sugar group has been modified. Such sugar modified nucleosides may impart enhanced nuclease stability, increased binding affinity or some other beneficial biological property to the oligomeric compounds. As used herein the term "modified sugar" refers to modifications that can be made to the furanose sugar portion of otherwise unmodified or modified nucleosides useful herein. Such modified sugars include without limitation substitution with one or more substituent groups, bridging of two non-geminal ring carbon atoms to form a bicyclic nucleoside or substitution of the 4'-O atom with a disubstituted methylene group [$C(R)_2$] or a heteroatom or substituted heteroatom (NR). Modified sugar moieties can also comprise mixtures of these modifications such as for example putting a 5'-substituent group on a bicyclic nucleoside.

In certain embodiments, examples of substituent groups useful for modifying furanose sugar moieties (e.g., sugar substituent groups used for nucleosides), include without limitation 2'-F, 2'-allyl, 2'-amino, 2'-azido, 2'-thio, 2'-O-allyl, 2'-OCF$_3$, 2'-O—C$_1$-C$_{10}$ alkyl, 2'-O—CH$_3$, OC$_3$, 2'-O—CH$_2$CH$_3$, 2'-O—(CH$_2$)$_2$CH$_3$, 2'-O—(CH$_2$)$_2$—O—CH$_3$ (MOE), 2'-O(CH$_2$)$_2$SCH$_3$, 2'-O—CH$_2$—CH═CH$_2$, 2'-O—(CH$_2$)$_3$—N(R$_m$)(R$_n$), 2'-O—(CH$_2$)$_2$—O—N(R$_m$)(R$_n$), 2'-O—(CH$_2$)$_2$—O—(CH$_2$)$_2$—N(R$_m$)(R$_n$), 2'-O—CH$_2$C(═O)—N(R$_m$)(R$_n$), 2'-O—CH$_2$C(═O)—N(H)—(CH$_2$)$_2$—N(R$_m$)(R$_n$) and 2'-O—CH$_2$—N(H)—C(═NR$_m$)[N(R$_m$)(R$_n$)], 5'-vinyl, 5'-methyl (R or S) and 4'-S wherein each R$_m$ and R$_n$ is, independently, H, substituted or unsubstituted C$_1$-C$_{10}$ alkyl or a protecting group. Further examples of modified sugar moieties include without limitation bicyclic sugars (e.g. bicyclic nucleic acids or bicyclic nucleosides discussed below).

Combinations of these modifications are also provided for herein without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group).

As used herein the terms "bicyclic nucleic acid" and "bicyclic nucleoside" refer to nucleosides wherein the sugar portion of the nucleoside is bicyclic (e.g. bicyclic sugar). In certain embodiments, a bicyclic nucleic acid comprises a nucleoside wherein the furanose ring comprises a bridge between two non-geminal ring carbon atoms. Examples of bicyclic nucleosides include without limitation nucleosides comprising a bridge between the 4' and the 2' ribosyl ring atoms. In certain embodiments, oligomeric compounds provided herein include one or more bicyclic nucleosides wherein the bridge comprises one of the formulae: 4'-(CH$_2$)—O-2'(LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., *J. Org. Chem.*, 2009, 74, 118-134); and 4'-CH$_2$—C(═CH$_2$)-2' (and analogs thereof see published International Application WO 2008/154401, published on Dec. 8, 2008). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated as is the case with the non-ring system used in peptide nucleic acid. The term is meant to include replacement of the sugar group with all manner of sugar surrogates know in the art and includes without limitation sugar surrogate groups such as morpholinos, cyclohexenyls and cyclohexitols. In most monomer subunits having a sugar surrogate group the heterocyclic base moiety is generally maintained to permit hybridization.

In certain embodiments, nucleosides having sugar surrogate groups include without limitation, replacement of the ribosyl ring with a surrogate ring system such as a tetrahydropyranyl ring system (also referred to as hexitol) as illustrated below:

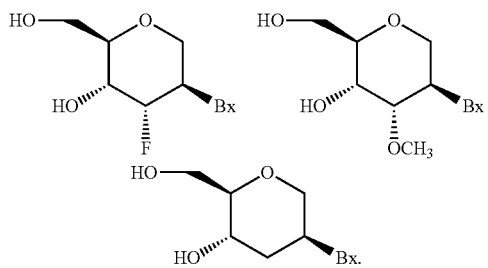

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J.). Such ring systems can undergo various additional substitutions to further enhance their activity.

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

Those skilled in the art, having possession of the present disclosure will be able to prepare oligomeric compounds, comprising a contiguous sequence of linked monomer subunits, of essentially any viable length to practice the methods disclosed herein. Such oligomeric compounds will include at least one and preferably a plurality of the base modified bicyclic nucleosides provided herein and may also include other monomer subunits including but not limited to nucleosides, modified nucleosides, nucleosides comprising sugar surrogate groups and nucleoside mimetics.

In certain embodiments, oligomeric compounds provided herein comprise from about 8 to about 80 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

In certain embodiments, oligomeric compounds provided herein comprise from about 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In certain embodiments, oligomeric compounds provided herein comprise from about 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In certain embodiments, oligomeric compounds provided herein comprise from about 8 to 16 monomer subunits in length. One having ordinary skill in the art will appreciate that this embodies oligomeric compounds of 8, 9, 10, 11, 12, 13, 14, 15 or 16 monomer subunits in length, or any range therewithin.

In certain embodiments, oligomeric compounds provided herein comprise from about 10 to 14 monomer subunits in length. One having ordinary skill in the art will appreciate that this embodies oligomeric compounds of 10, 11, 12, 13 or 14 monomer subunits in length, or any range therewithin.

In certain embodiments, oligomeric compounds provided herein comprise from about 10 to 18 monomer subunits in length. One having ordinary skill in the art will appreciate that this embodies oligomeric compounds of 10, 11, 12, 13, 14, 15, 16, 17 or 18 monomer subunits in length, or any range therewithin.

In certain embodiments, oligomeric compounds provided herein comprise from about 10 to 21 monomer subunits in length. One having ordinary skill in the art will appreciate that this embodies oligomeric compounds of 10, 11, 12, 13, 14, 15, 16, 17, 18, 19, 20 or 21 monomer subunits in length, or any range therewithin.

In certain embodiments, oligomeric compounds provided herein comprise from about 12 to 14 monomer subunits in length. One having ordinary skill in the art will appreciate that this embodies oligomeric compounds of 12, 13 or 14 monomer subunits in length, or any range therewithin.

In certain embodiments, oligomeric compounds provided herein comprise from about 12 to 18 monomer subunits in length. One having ordinary skill in the art will appreciate that this embodies oligomeric compounds of 12, 13, 14, 15, 16, 17 or 18 monomer subunits in length, or any range therewithin.

In certain embodiments, oligomeric compounds provided herein comprise from about 12 to 21 monomer subunits in length. One having ordinary skill in the art will appreciate that this embodies oligomeric compounds of 12, 13, 14, 15, 16, 17, 18, 19, 20 or 21 monomer subunits in length, or any range therewithin.

In certain embodiments, oligomeric compounds provided herein comprise from about 14 to 18 monomer subunits in length. One having ordinary skill in the art will appreciate that this embodies oligomeric compounds of 14, 15, 16, 17 or 18 monomer subunits in length, or any range therewithin.

In certain embodiments, oligomeric compounds of any of a variety of ranges of lengths of linked monomer subunits are provided. In certain embodiments, oligomeric compounds are provided consisting of X-Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, this provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-27, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, the ranges for the oligomeric compounds listed herein are meant to limit the number of monomer subunits in the oligomeric compounds, however such oligomeric compounds may further include 5' and/or 3'-terminal groups including but not limited to protecting groups such as hydroxyl protecting groups, optionally linked conjugate groups and/or other substituent groups.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, *Methods*, 2001, 23, 206-217; Gait et al., *Applications of Chemically synthesized RNA in RNA: Protein Interactions*, Smith, Ed., 1998, 1-36; Gallo et al., *Tetrahedron*, 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in *Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—CH$_2$—O—Si(iPr)$_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O-[1(2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

As used herein the term "hybridization" includes the pairing of complementary strands of oligomeric compounds such as including the binding of an oligomeric compound as provided herein to a target nucleic acid. In certain embodiments, the mechanism of pairing involves hydrogen bonding, which may be Watson-Crick, Hoogsteen or reversed Hoogsteen hydrogen bonding, between complementary heterocyclic base moieties of nucleosides (or monomer subunits) that are in close enough proximity to hydrogen bond. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid resulting in a loss of activity. To be specifically hybridizable also requires a sufficient degree of complementarity to avoid non-specific binding of the oligomeric compound to non-target nucleic acid sequences under the conditions in which specific binding is desired, i.e., under physiological conditions (for in vivo assays or therapeutic treatment) or other diagnostic conditions (for performing in vitro assays).

As used herein the term "complementary," refers to the capacity for precise pairing of two nucleobases regardless of where the two nucleobases are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between an oligomeric compound and its target nucleic acid.

It is understood in the art that the sequence of an oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., *J. Mol. Biol.,* 1990, 215, 403-410; Zhang and Madden, *Genome Res.,* 1997, 7, 649-656).

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds provided herein may elicit the action of one or more enzymes or structural proteins to effect modification of the target nucleic acid. Alternatively, the oligomeric compound may inhibit the activity the target nucleic acid through an occupancy-based method, thus interfering with the activity of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent. In the case of oligomeric compounds targeted to microRNA, candidate modulators may be evaluated by the extent to which they increase the expression of a microRNA target RNA or protein (as interference with the activity of a microRNA will result in the increased expression of one or more targets of the microRNA).

Suitable target segments may also be combined with their respective complementary oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature,* 1998, 391, 806-811; Timmons and Fire, *Nature,* 1998, 395, 854; Timmons et al., *Gene,* 2001, 263, 103-112; Tabara et al., *Science,* 1998, 282, 430-431; Montgomery et al., *Proc. Natl. Acad. Sci. USA,* 1998, 95, 15502-15507; Tuschl et al., *Genes Dev.,* 1999, 13, 3191-3197; Elbashir et al., *Nature,* 2001, 411, 494-498; Elbashir et al., *Genes Dev.,* 2001, 15, 188-200). For example, such double-stranded moieties have been shown to inhibit the target by the classical hybridization of antisense strand of the duplex to the target, thereby triggering enzymatic degradation of the target (Tijsterman et al., *Science,* 2002, 295, 694-697).

The oligomeric compounds provided herein can also be applied in the areas of drug discovery and target validation. In certain embodiments, provided herein is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound as provided herein. These methods can also be performed in parallel or in combination with other experiments to determine the function of unknown genes for the process of target validation or to determine the validity of a particular gene product as a target for treatment or prevention of a particular disease, condition, or phenotype. In certain embodiments, oligomeric compounds are provided for use in therapy. In certain embodiments, the therapy is reducing target messenger RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds are provided herein that may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., *Nature*, 2001, 411, 494-498; Nishikura et al., *Cell*, 2001, 107, 415-416; and Bass et al., *Cell*, 2000, 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or other therapeutics as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of oligomeric compounds as provided herein, particularly the primers and probes, with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more of the oligomeric compounds provided herein are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. USA*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

While in certain embodiments, oligomeric compounds provided herein can be utilized as described, the following examples serve only to illustrate and are not intended to be limiting.

EXAMPLE 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

EXAMPLE 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3-H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M $NH_4OAc$ solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. Nos. 5,610,289 or 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

EXAMPLE 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M $NH_4OAc$ with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32 +/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

EXAMPLE 4

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3-H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

EXAMPLE 5

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

EXAMPLE 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 μg/mL per 100 nM oligomeric compound(s). This transfection mixture is incubated at room temperature for approximately 0.5 hours. For cells grown in 96-well plates, wells are washed once with 100 μL OPTI-MEM™-1 and then treated with 130 μL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPO-FECTAMINE™, OLIGOFECTAMINE™, and FUGENE™. Other suitable transfection methods known in the art include, but are not limited to, electroporation.

EXAMPLE 7

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/-extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 μL of RIBOGREEN™ working reagent (RIBOGREEN™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

EXAMPLE 8

Analysis of Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired.

RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

EXAMPLE 9

Design of Phenotypic Assays and in vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In vivo Studies

The individual subjects of the in vivo studies described herein are warm-blooded vertebrate animals, which includes humans.

EXAMPLE 10

RNA Isolation

Poly(A)+ mRNA Isolation

Poly(A)+ mRNA is isolated according to Miura et al., (Clin. Chem., 1996, 42, 1758-1764). Other methods for poly (A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 μL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

EXAMPLE 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
Forward primer:                    (SEQ ID NO: 2)
AATGGCTAAGTGAAGATGACAATCAT Reverse primer:                    (SEQ ID NO: 3)
TGCACATATCATTACACCAGTTCGT
```

And the PCR probe:
FAM-TTGCAGCAATTCACTGTAAAGCTG-GAAAGG-TAMRA (SEQ ID NO: 4), where FAM is the fluorescent dye and TAMRA is the quencher dye.

EXAMPLE 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

EXAMPLE 13

Preparation of Compounds 6 and 7

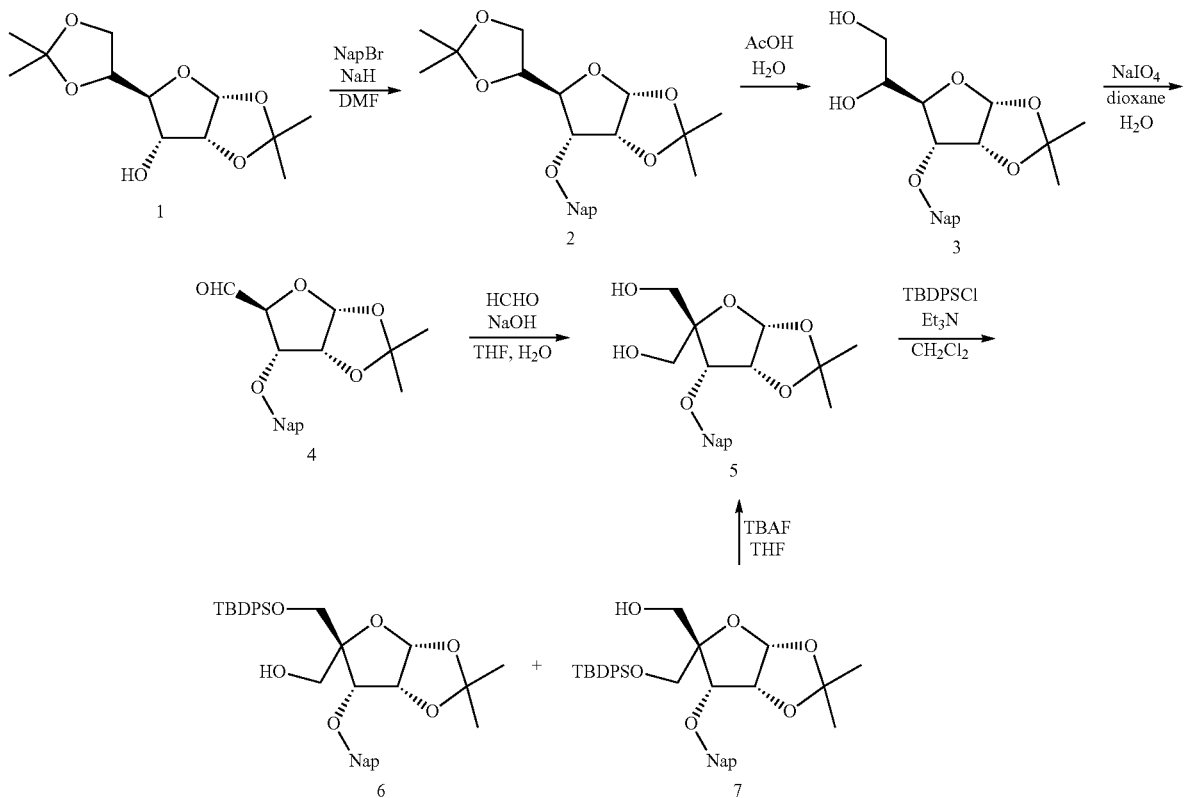

Nap = 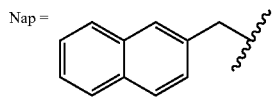

a) Preparation of Compound 2

Compound 1 (135 g, 519.0 mmol, commercially available) and 2-(bromomethyl)-naphthalene (126 g, 570.0 mmol) were dissolved in DMF (500 mL) in a three-necked flask (500 mL) and the reaction was cooled in an ice bath. Sodium hydride (60% w/w, 29 g, 727.0 mmol) was carefully added (6 g portions every 10 minutes) to the reaction and the stirring was continued for another 60 minutes after the addition was complete. At this time TLC analysis showed no more starting Compound 1. The reaction was carefully poured onto crushed ice (ca. 500 g) and the resulting slurry was stirred vigorously until all the ice melted. The resulting off-white solid was collected by filtration and suspended in water. The suspension was stirred vigorously using a mechanical stirrer for 30 minutes after which the solid was collected by filtration and suspended in hexanes. The suspension was stirred vigorously for 30 minutes after which the solid was collected by filtration and air dried for 4-6 hours and then dried under high vacuum over $P_2O_5$ for 16 hours to provide Compound 2 (206.0 g, 99%) as an off-white solid.

Compound 2 $^1$H NMR (300 MHz, $CDCl_3$) δ: 7.85 (m, 4H), 7.48 (m, 3H), 5.74 (s, 1H), 4.92 (d, 1H, J=11.7), 4.75 (d, 1H, J=11.6), 4.58 (m, 1H), 4.36 (m, 1H), 4.15 (m, 1H), 4.03-3.86 (m, 3H), 1.61 (s, 3H), 1.36 (s, 9H).

b) Preparation of Compound 3

Compound 2 (200.0 g, 0.5 moles) was added in small portions to a solution of acetic acid (2.2 L) and water (740 mL). The reaction was stirred at room temperature for 16 h after which, TLC analysis (30% EtOAc/hexanes) indicated complete consumption of Compound 2. The reaction was then concentrated under reduced pressure until most of the acetic acid was removed. The remaining solution was poured into a stirred mixture of EtOAc (1 L) and water (1 L). Solid KOH was then added to the above mixture until the aqueous layer was strongly basic (pH>12). The organic layer was then separated, washed with saturated sodium bicarbonate solution, brine, dried ($Na_2SO_4$), filtered and concentrated under reduced pressure to provide Compound 3 as a yellow foam, which was used without any further purification.

c) Preparation of Compound 4

A solution of $NaIO_4$ (107.0 g) in water (3 L) was added over 40 minutes to a stirred (mechanical stirrer) solution of Compound 3 (crude from above) in dioxane (1.5 L). After 60 minutes the reaction mixture was poured into EtOAc (1.5 L) and the organic layer was separated, washed with water (1 L), brine (1 L), dried ($Na_2SO_4$) and concentrated to provide Compound 4 as a yellow oil, which was used without any further purification.

d) Preparation of Compound 5

Compound 4 (crude from above) was dissolved in a mixture of THF (500) and water (500 mL) and the reaction was cooled in an ice bath. 2N NaOH (600 mL) and formaldehyde (250 mL of a 37% aqueous solution) were added to the reaction and the stirring was continued at room temperature for 3 days. The reaction was then poured into EtOAc (1 L) and washed with water (1 L), brine (1 L) and evaporated under reduced pressure until approximately 200 mL of EtOAc was left (a white precipitate was formed in the process). Hexanes (300 mL) was added to the precipitate and the mixture was allowed to stand for 16 hours after which the white solid was collected by filtration, washed with hexanes and dried under high vacuum over $P_2O_5$ to provide Compound 5 as a white solid (124 g, 66% from Compound 2).

Compound 5 $^1$H NMR (300 MHz, $CDCl_3$) δ: 7.85 (m, 4H), 7.48 (m, 3H), 5.75 (d, 1H, J=3.9), 4.96 (d, 1H. J=11.8), 4.75 (d, 1H, J=11.8), 4.66 (m, 1H), 4.26 (d, 1H, J=5.2), 3.95 (m, 2H), 3.79 (m, 1H), 3.63 (m, 1H), 2.39 (m, 1H, OH), 1.66 (s, 3H), 1.34 (s, 3H).

e) Preparation of Compounds 6 and 7 tert-Butyldiphenylchlorosilane (305.0 mmol, 84.0 mL) was added to a cold (0° C.) stirring solution of Compound 5 (278.0 mmol, 100.0 g) and triethylamine (305 mmol, 43.0 mL) in dichloromethane (600 mL). After the addition was complete, the reaction was warmed to room temperature and the stirring was continued for 16 hours. MeOH (50 mL) was added (to quench the excess TBDPSCl) to the reaction and the stirring was continued for another 2 hours at room temperature. The reaction was then diluted with chloroform and the organic layer was washed with 10% HCl, saturated $NaHCO_3$, brine, dried ($Na_2SO_4$) and concentrated to provide a thick oil. Hexanes (150 mL) was added to the oil and the mixture was sonicated until a solution resulted. The solution was now seeded with a small amount of Compound 6 (previously isolated by column chromatography). After standing for 16 hours additional hexanes was added to the thick slurry and the solid was collected by filtration. The solid was then resuspended in hexanes and stirred vigorously for 30 minutes. The solid was collected by filtration and dried under high vacuum for 16 h to provide Compound 6 (80.5, 48% g). The filtrates were combined and concentrated under reduced pressure. The resulting oil was redissolved in minimum amount of hexanes and passed through a plug of silica gel (eluting with 20% EtOAc in hexanes). Fractions containing Compound 6 were combined, concentrated and crystallized as described above to provide a second crop of Compound 6 (20 g, 12%) as a white solid. Further elution of the silica gel plug with 50% EtOAc in hexanes provided pure Compound 6 (40.0 g, 24%) as a thick oil. In addition, a mixture of Compounds 6 and 7 (ca 15 g, 9%) was also isolated as a thick oil.

Compound 6 $^1$H NMR (300 MHz, $CDCl_3$) δ: 7.83 (m, 4H), 7.56 (m, 7H), 7.30 (m, 6H), 5.80 (s, 1H), 4.97 (d, 1H, J=11.4), 4.70 (m, 2H), 4.46 (m, 1H), 3.92-3.66 (m, 4H), 2.39 (m, 1H, OH), 1.67 (s, 3H), 1.37 (s, 3H), 0.92 (s, 9H).

Compound 7; $^1$H NMR (300 MHz, $CDCl_3$) δ: 7.9-7.3 (m, 17H), 5.71 (d, 1H, J=3.9), 4.86 (d, 1H, J=12.2), 4.74 (d, 1H, J=12.2), 4.56 (m, 1H), 4.22 (d, 1H, J=11.1), 4.18 (m, 1H), 4.07 (d, 1H, J=11.1), 4.02 (dd, 1H, J=4.2, 12.0), 3.64 (dd, 1H, J=9.4, 11.9), 1.89 (m, 1H), 1.25 (s, 6H), 1.05 (s, 9H).

f) Recovery of Compound 5 from Compound 7

Tetrabutylammonium fluoride (70 mL of a 1 M solution in THF) was added to a cold (0° C.) stirring solution of Compound 7 (62.7 mmol, 37.5 g) in THF (250 mL) after which, the reaction was allowed to warm to room temperature gradually. After stirring for an additional 72 hours, the reaction was concentrated under vacuum and the residue was poured onto crushed ice. The flask was rinsed with some additional THF (3 times) and added to the above suspension. The supernatant was removed by decantation and the solid at the bottom was added to a stirring mixture of hexanes (200 mL) and water (200 mL). After stirring for 2 hours, the flocculent solid was collected by filtration, washed with additional water and hexanes and dried under high vacuum to provide Compound 5 (20 g, 89%) as a white solid.
EXAMPLE 14
Preparation of Compound 17
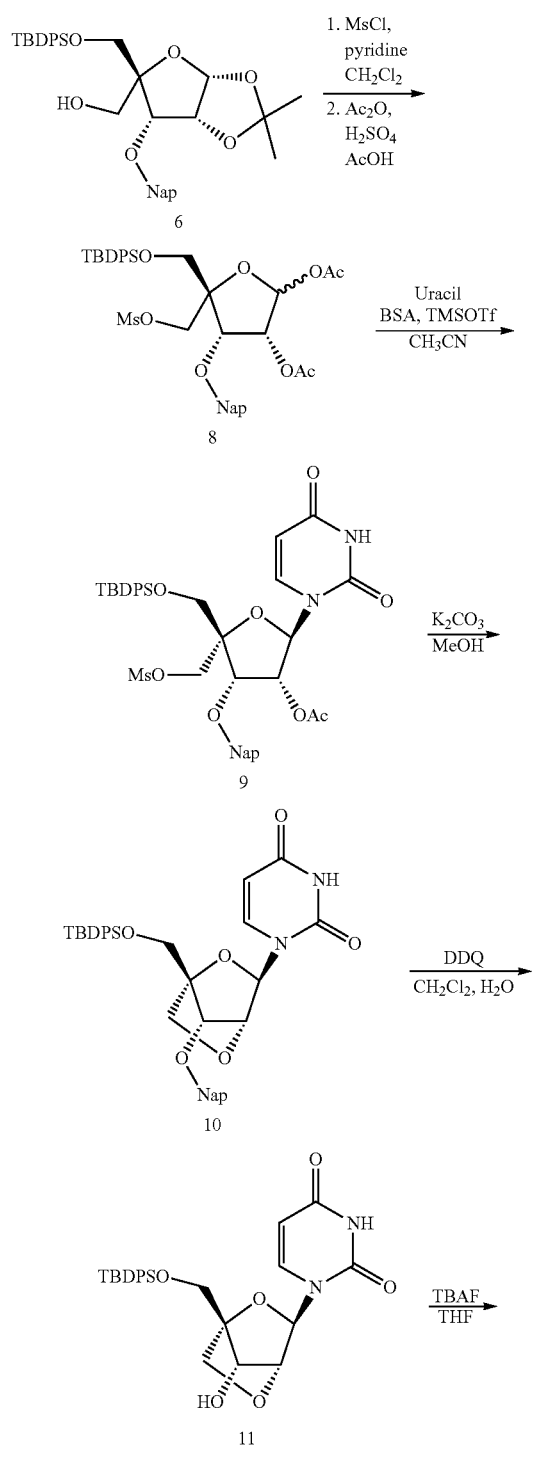
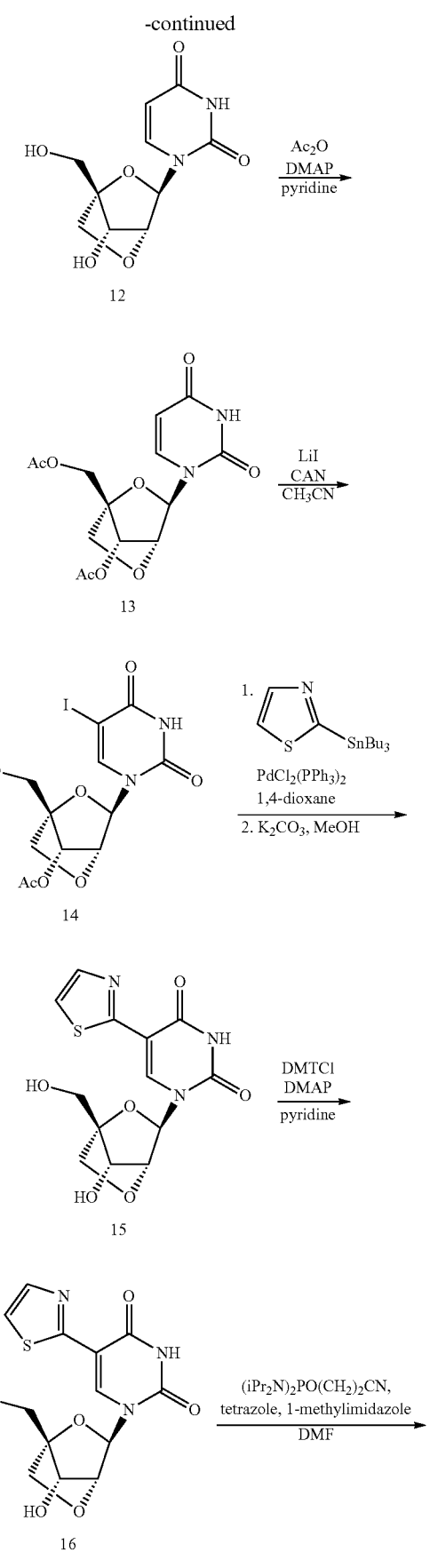

-continued

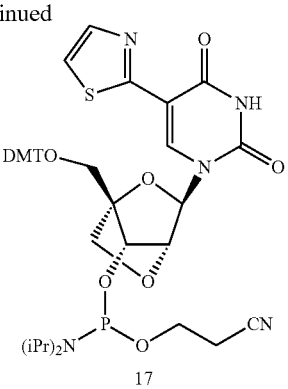

17 a) Preparation of Compound 8

Compound 6 was prepared per the procedures illustrated in Example 13. Methane-sulfonyl chloride (5.28 mL, 68.2 mmol) was added to a solution of Compound 6 (25.5 g, 42.6 mmol) in a mixture of anhydrous $CH_2Cl_2$ (200 mL) and anhydrous pyridine (150 mL). After stirring at ambient temperature for 2 h, the mixture was concentrated in vacuo to yield a residue which was resuspended in ethyl acetate (500 mL) and washed with half-saturated $NaHCO_3$ (3×500 mL). The organic layer was dried over anhydrous $Na_2SO_4$, filtered, and concentrated to yield the crude mesylate (28.9 g, quant) as a pale foam, which was used without further purification.

Acetic anhydride (30 mL) and concentrated $H_2SO_4$ (1 mL) were added to a solution of the crude mesylate from above (28.8 g, 42.5 mmol) in glacial acetic acid (125 mL). After stirring at ambient temperature for 2 h, the reaction mixture was concentrated in vacuo. The resulting thick oil residue was redissolved in ethyl acetate (500 mL) and carefully washed with saturated aqueous $NaHCO_3$ (3×500 mL) until the pH reached neutral. The organic layer was dried over anhydrous $Na_2SO_4$, filtered, and concentrated to provide an anomeric mixture of diacetate, Compound 8 (30.2 g, 98.4% from Compound 6) as a pale oil. $^1H$ NMR analysis showed an approximately 8:1 anomeric mixture of diacetate, Compound 8.

b) Preparation of Compound 9

N,O-bis-trimethylsilyl acetamide (47.8 mL, 195 mmol) was added to a suspension of Compound 8 (29.98 g, 41.59 mmol) and uracil (6.99 g, 62.4 mmol) in anhydrous $CH_3CN$ (236 mL). After heating at 55° C. for 1.5 h to get a homogeneous solution, the reaction mixture was cooled to 0° C. and trimethylsilyl triflate (15.0 mL, 83.2 mmol) was added. After stirring at 55° C. for another 5.5 h, the reaction mixture was cooled to 0° C. and carefully quenched with saturated aqueous $NaHCO_3$ (dropwise) until a white precipitate persisted. The mixture was concentrated in vacuo and the resulting thick white residue was resuspended in ethyl acetate (500 mL), washed with half-saturated aqueous $NaHCO_3$ (3×500 mL), dried over anhydrous $Na_2SO_4$, filtered, concentrated and dried to provide crude Compound 9 (30.8 g, 95.9%) as a pale yellow foam, which was used without further purification.

c) Preparation of Compound 10

Potassium carbonate (11.1 g, 80 mmol) was added to a solution of Compound 9 (29.4 g, 38.1 mmol) in anhydrous methanol (350 mL). After stirring at ambient temperature for 5 h, the reaction mixture was concentrated under reduced pressure. The residue was dissolved in ethyl acetate (1 L) and the organic layer was washed with saturated aqueous $NaHCO_3$ (2×1 L), dried over anhydrous $Na_2SO_4$, filtered, and concentrated. Purification by column chromatography (silica gel, eluting with 1% methanol in $CH_2Cl_2$) provided Compound 10 (20.0 g, 82.8%) as a pale yellow foam.

d) Preparation of Compound 11

DDQ (15.9 g, 70.0 mmol) was added to a solution of Compound 10 (19.7 g, 31.1 mmol) in a mixture of $CH_2Cl_2$ (200 mL) and water (40 mL). After stirring vigorously at ambient temperature, the biphasic mixture was diluted with $CH_2Cl_2$ up to a total volume of 1 L, then washed with 1% (w/v) aqueous $NaHSO_3$ (2×1 L), and half-saturated aqueous $NaHCO_3$ (1×1 L). The combined organic layers were dried over anhydrous $Na_2SO_4$, filtered, and concentrated under reduced pressure. Purification by column chromatography (silica gel, eluting with 2.5% methanol in $CH_2Cl_2$) provided Compound 11 (15.0 g, 97.4%) as an off-white foam. ESI-MS $[M+H^+]$: calc. 495 Da; obs. 495 Da.

e) Preparation of Compound 12

Tetrabutylammonium fluoride (29.4 mmol, 29.4 mL of 1 M solution in THF) was added to a solution of Compound 11 (13.2 g, 26.7 mmol) in anhydrous THF (60 mL) with stirring at ambient temperature for 2 h. The solvent was removed under reduced pressure and the resulting thick oil was redissolved in a minimum amount of $CH_2Cl_2$, then purified by column chromatography (silica gel, eluting with 10% methanol in $CH_2Cl_2$). The product-containing fractions were combined and concentrated in vacuo to provide a pale solid which was resuspended in minimum amount of ice cold methanol. The resulting solid was collected by filtration and dried under vacuum to furnish Compound 12 (5.79 g, 84.6%). ESI-MS $[M+H^+]$: calc. 257 Da; obs. 257 Da.

f) Preparation of Compound 13

DMAP (0.59 g, 4.9 mmol) and acetic anhydride (5.5 mL, 58.6 mmol) were added to a solution of Compound 12 (5.00 g, 19.5 mmol) in anhydrous pyridine (60 mL). After stirring at ambient temperature for 2.5 h, the solvent was removed under reduced pressure. The resulting residue was redissolved in $CH_2Cl_2$ (350 mL), washed with half-saturated aqueous $NaHCO_3$ (2×300 mL), dried over anhydrous $Na_2SO_4$, filtered and concentrated. Purification by column chromatography (silica gel, eluting with 2% methanol in $CH_2Cl_2$) provided Compound 13 (5.83 g, 87.7%) as a white foam.

g) Preparation of Compound 14

Lithium iodide (2.01 g, 15.0 mmol) and ammonium cerium (IV) nitrate (14.9 g, 27.3 mmol) were added to a solution of Compound 13 (4.65 g, 13.7 mmol) in anhydrous $CH_3CN$ (60 mL). After stirring at 85° C. for 3 h, the reaction was allowed to cool to room temperature and the resulting solid was filtered through a glass frit. The filtrate was concentrated in vacuo to provide a thick oil, which was then resuspended in a minimal amount of 5% methanol in $CH_2Cl_2$ solution. The mixture was heated and sonicated until a solution resulted followed by purification (silica gel, eluting with 1% methanol in $CH_2Cl_2$) to furnish Compound 14 (6.43 g, quant) as a white solid. ESI-MS $[M+H^+]$: calc. 467 Da; obs. 467 Da.

h) Preparation of Compound 15

Tributyltin thiazole (12.0 mL, 38.6 mmol) followed by $PdCl_2(PPh_3)_2$ (3.87 g, 5.51 mmol) was added to a solution of Compound 14 (6.42 g, 13.8 mmol) in 1,4-dioxane (160 mL). After stirring at 85° C. for 7 h, the reaction was concentrated under reduced pressure until the total volume reached 30 mL. Methanol (150 mL) and $K_2CO_3$ (5.0 g, 35.7 mmol) were then added to this mixture and the stirring was continued at ambient temperature for 12 h. The resulting precipitates were isolated, washed with 5% methanol in $CH_2Cl_2$, and dried under vacuum to provide Compound 15 (2.95 g, quant) as an off-white solid. ESI-MS $[M+H^+]$: calc. 340 Da; obs. 340 Da.

i) Preparation of Compound 16

DMAP (0.18 g, 1.44 mmol) and 4,4'-dimethoxytrityl chloride (4.89 g, 14.4 mmol) were added to a suspension of Compound 15 (3.26 g, 9.63 mmol) in anhydrous pyridine (40 mL). After stirring at room temperature for 3 h, methanol (5 mL) was added to the reaction to quench excess DMTCl and concentrated in vacuo. The resulting thick oil was redissolved in $CH_2Cl_2$ (500 mL) and washed with half-saturated $NaHCO_3$ (2×500 mL). The organic layer was dried over anhydrous $Na_2SO_4$, filtered and concentrated. Purification by column chromatography (silica gel, eluting with 2% methanol in $CH_2Cl_2$) provided Compound 16 (3.43 g, 56%) as a blue-gray foam.

j) Preparation of Compound 17

Tetrazole (78 mg, 1.11 mmol), 1-methylimidazole (44 µL, 0.55 mmol), and 2-cyanoethyl-N,N,N',N'-tetraisopropylaminophosphorodiamidite (1.05 mL, 3.32 mmol) were added to a solution of Compound 16 (1.42 g, 2.21 mmol) in anhydrous DMF (5.6 mL). After stirring at ambient temperature for 4 h, triethylamine (1.23 mL, 8.85 mmol) was added. The reaction mixture was poured into ethyl acetate (200 mL) and washed with half-saturated $NaHCO_3$ (2×200 mL), dried over anhydrous $Na_2SO_4$, filtered, and concentrated. The resulting oil was purified by column chromatography (silica gel, eluting with 1:1 hexanes:ethyl acetate) to provide Compound 17 (1.61 g, 86.4%) as a pale foam. $^1H$ and $^{31}P$ NMR analysis showed an approximately 3:1 mixture of phosphorous diastereomers.

EXAMPLE 15

Preparation of Compound 21

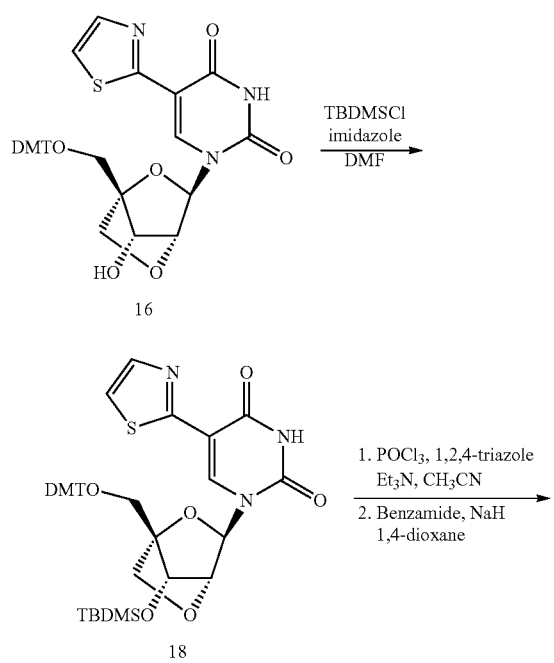

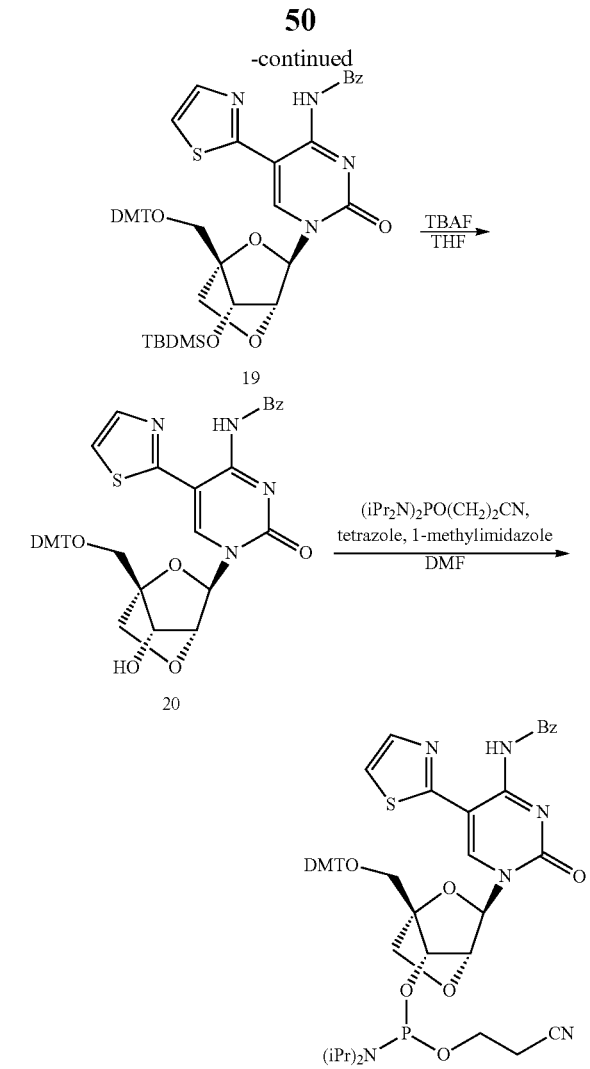

a) Preparation of Compound 18

Imidazole (1.59 g, 23.4 mmol) followed by tert-butyldimethylsilyl chloride (1.17 g, 7.78 mmol) was added to a solution of Compound 16 (1.99 g, 3.11 mmol) in anhydrous DMF (15 mL). After stirring at ambient temperature for 20 h, the mixture was poured into ethyl acetate (250 mL) and washed with half-saturated aqueous $NaHCO_3$ (250 mL), water (2×200 mL), dried over anhydrous $Na_2SO_4$, filtered, and concentrated. Purification by column chromatography (silica gel, eluting with 2:1 hexanes:ethyl acetate) provided Compound 18 (2.15 g, 91.2%) as an off-white foam.

b) Preparation of Compound 19

Phosphorous oxychloride (1.04 mL, 11.1 mmol) was added dropwise to an ice cold suspension of 1,2,4-triazole (2.69 g, 39.0 mmol) in $CH_3CN$ (35 mL). While maintaining the temperature at 0° C., the resulting slurry was treated with triethylamine (7.75 mL, 55.6 mmol) to form a thick slush and a solution of Compound 18 (2.10 g, 2.78 mmol) in $CH_3CN$ (16 mL) was added. The reaction mixture was allowed to warm to room temperature and the stirring was continued for another 3 h. The reaction was then diluted with ethyl acetate (300 mL) and washed with half-saturated aqueous $NaHCO_3$ (2×200 mL), dried over anhydrous $Na_2SO_4$, filtered, and concentrated. The resulting yellow foam was redissolved in anhydrous 1,4-dioxane (22 mL) and cannulated to a mixture of benzamide (2.02 g, 16.7 mmol) and sodium hydride (0.56 g of a 60% mineral oil dispersion, 13.9 mmol) in 1,4-dioxane (22 mL) that was previously prepared. After 2 h, the reaction mixture was poured into ethyl acetate (250 mL) and washed with half-saturated aqueous NaHCO$_3$ (2×200 mL), dried over anhydrous Na$_2$SO$_4$, filtered, and concentrated. Purification by column chromatography (silica gel, eluting with 2:1 hexanes:ethyl acetate) provided Compound 19 (2.03 g, 84.9%) as an off-white foam. ESI-MS [M−H$^+$]: calc. 858 Da; obs. 858 Da. $^1$H NMR analysis showed Compound 19 existed as an approximately 4:1 mixture of rotational isomers around the C5-thiazole bond.

c) Preparation of Compound 20

Tetrabutylammonium fluoride (2.46 mmol, 2.46 mL of a 1 M solution in THF) was added to a solution of Compound 19 (2.01 g, 2.34 mmol) in anhydrous THF (5 mL). After stirring at room temperature for 3.5 h, the mixture was concentrated under reduced pressure and purified by column chromatography (silica gel, eluting with 1% methanol in CH$_2$Cl$_2$) to furnish Compound 20 (1.57 g, 90%) as a pale yellow foam. ESI-MS [M−H$^+$]: calc. 743 Da; obs. 743 Da. Structural analysis of Compound 20 was confirmed by $^1$H NMR and the line-broadening suggested interconversion of the C5-thiazole rotational isomers.

d) Preparation of Compound 21

Tetrazole (71 mg, 1.01 mmol), 1-methylimidazole (40 µL, 0.51 mmol), and 2-cyanoethyl-N,N,N',N'-tetraisopropylaminophosphorodiamidite (0.97 mL, 3.04 mmol) were added to a solution of Compound 20 (1.51 g, 2.03 mmol) in anhydrous DMF (5.1 mL). After stirring at ambient temperature for 3 h, triethylamine (1.13 mL, 8.12 mmol) was added. The reaction was then poured into ethyl acetate (125 mL) and washed with half-saturated NaHCO$_3$ (3×100 mL), dried over anhydrous Na$_2$SO$_4$, filtered, and concentrated. Purification by column chromatography (silica gel, eluting with 1:1 hexanes:ethyl acetate) provided Compound 21 (1.80 g, 93.8%) as a pale yellow foam. $^1$H and $^{31}$P NMR analysis showed a mixture of both phosphorous diastereomers and C5-thiazole rotational isomers.

EXAMPLE 16

Preparation of Compound 24

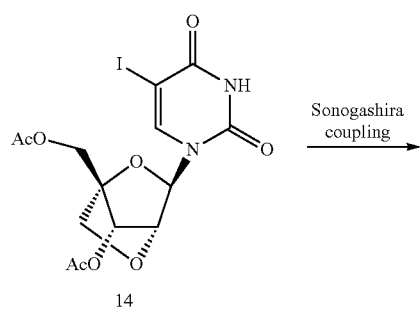

14

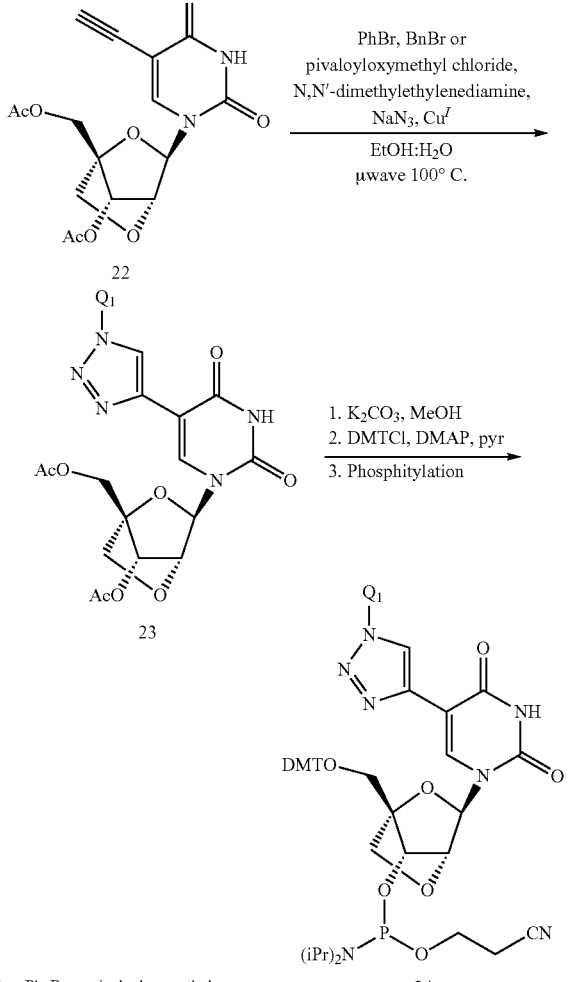

$Q_1$ = Ph, Bn or pivaloyloxymethyl

Compound 14 is prepared per the procedure illustrated in Example 14. 5-ethynyl pyrimidine Compound 22 and phosphoramidite Compound 24 are prepared using modifications of published procedures reported by Nielsen, P. *Chem Bio Chem* 2007, 8, 2106-2116. Compound 22 can also be used as a general building block to introduce an aromatic ring at the C5-position of a pyrimidine base.

EXAMPLE 17

General Preparation of Compound 27

-continued

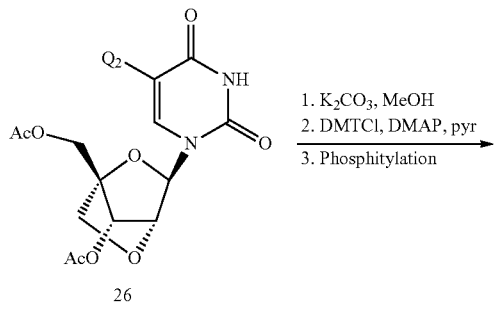

26

1. K₂CO₃, MeOH
2. DMTCl, DMAP, pyr
3. Phosphitylation
→

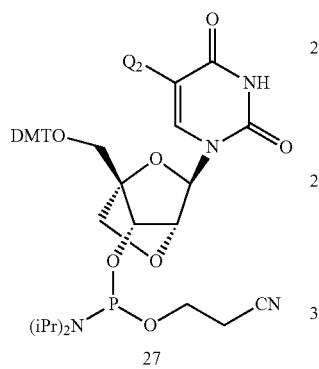

27

Q2 is an aryl, substituted aryl, heteroaryl or substituted heteroaryl ring system comprising from 5 to 7 ring atoms independently selected from C, N, O and S.

Compound 14 is prepared per the procedure illustrated in Example 14. Stannanes Compound 25 and phosphoramidite Compound 27 are prepared using modifications of published procedures reported by Froehler, B. C. *J. Am. Chem. Soc.* 1994, 116, 5540-5544 and references therein.

EXAMPLE 18

General Preparation of Compound 31

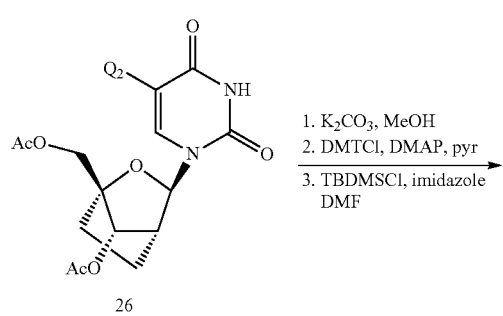

26

1. K₂CO₃, MeOH
2. DMTCl, DMAP, pyr
3. TBDMSCl, imidazole DMF
→

-continued

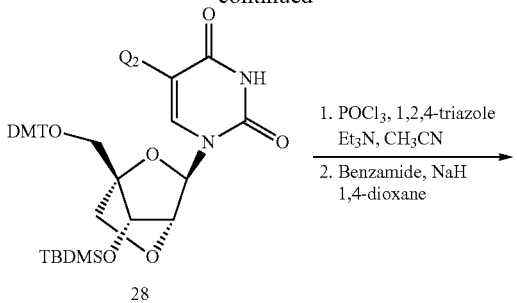

28

1. POCl₃, 1,2,4-triazole Et₃N, CH₃CN
2. Benzamide, NaH 1,4-dioxane
→

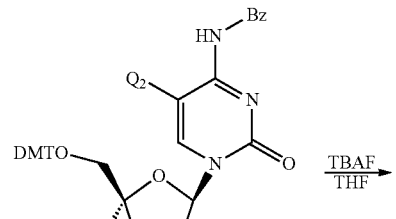

29

TBAF/THF →

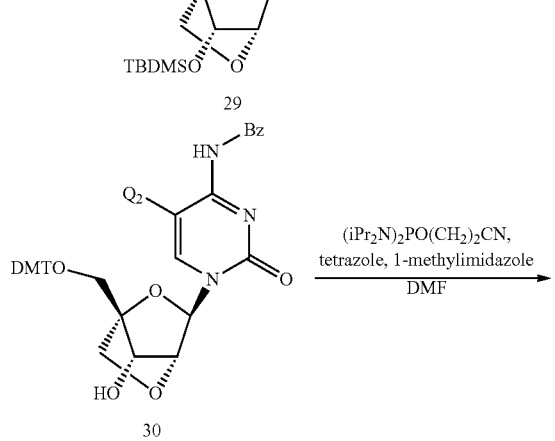

30

(iPr₂N)₂PO(CH₂)₂CN, tetrazole, 1-methylimidazole DMF →

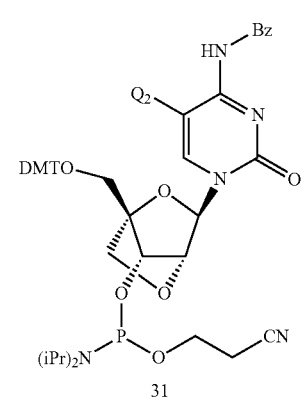

31

$Q_2$ is an aryl, substituted aryl, heteroaryl or substituted heteroaryl ring system comprising from 5 to 7 ring atoms independently selected from C, N, O and S.

Compound 26 is prepared per the general procedure illustrated in Example 17.

EXAMPLE 19

In Vivo PTEN Study, Single Dose Administration

Six week old Balb/c mice (Jackson Laboratory, Bar Harbor, Me.) were injected (i.p.) once with one of the gapped oligomeric compounds (ISIS 392056 or ISIS 403737) targeted to PTEN at a dose of 2.5, 5, 10 or 20 μmol/kg (ISIS 392056 not dosed at the 20 μmol/kg dose). The mice were sacrificed 48 hours following injection. Liver tissues were homogenized and mRNA levels were quantitated using real-time PCR as per procedures described herein for comparison to untreated control (% UTC). Plasma chemistry analysis was also completed. The results are listed below as the average % of the PTEN mRNA expression for each treatment group relative to the saline-injected control. Liver transaminase levels, alanine aminotranferease (ALT) and aspartate aminotransferase (AST), in serum were also measured relative to saline injected mice. The approximate liver transaminase levels are listed in the table below.

| SEQ. ID NO./ ISIS NO. | Composition (5' to 3') | Motif |
|---|---|---|
| 05/392056 | $T_l{}^{Me}C_l$ATGGCTGCAG$^{Me}C_l T_l$ | 4'-CH$_2$-O-2' BNA |
| 06/403737 | $^{Th}U_l{}^{Th}C_l$ATGGCTGCAG$^{Th}C_l{}^{Th}U_l$ | 5-thiazole BNA |

All internucleoside linkages are phosphorothioate. Nucleosides not followed by a subscript are β-D-2'-deoxyribonucleosides. Annotated nucleosides are described below.

The body weights, liver weights, spleen weights and kidney weights were comparable for the different doses of ISIS 392056 and ISIS 403737 with no substantial deviations compared to the saline treated animals.

EXAMPLE 20

In Vivo PTEN Study, Multiple Dose Administration

Six week old Balb/c mice (Jackson Laboratory, Bar Harbor, Me.) were injected (i.p) twice per week for three weeks with gapped oligomeric compounds (ISIS 392063 or 403736) targeted to PTEN at a dose of 0.1, 0.32, 1 or 3.2 μmol/kg. The mice were sacrificed 48 hours following the last administration. Liver tissues were homogenized and mRNA levels were quantitated using real-time PCR as per procedures described herein for comparison to untreated control (% UTC). Plasma chemistry analysis was also completed. Estimated ED$_{50}$ concentrations for each oligomeric compound were calculated using Graphpad Prism and are listed below. Liver transaminase levels, alanine aminotransferease (ALT) and aspartate aminotransferase (AST), in serum were also measured relative to saline injected mice. The approximate liver transaminase levels are listed in the table below.

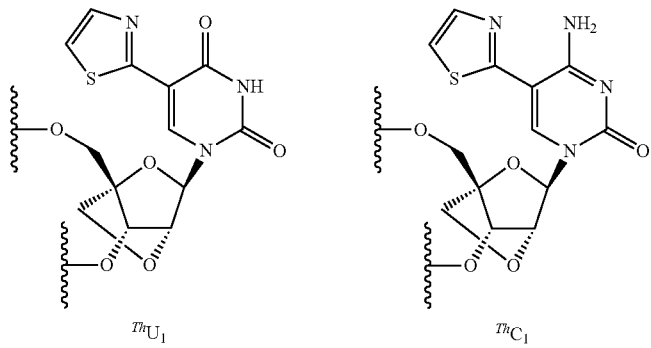

$^{Th}U_l$        $^{Th}C_l$

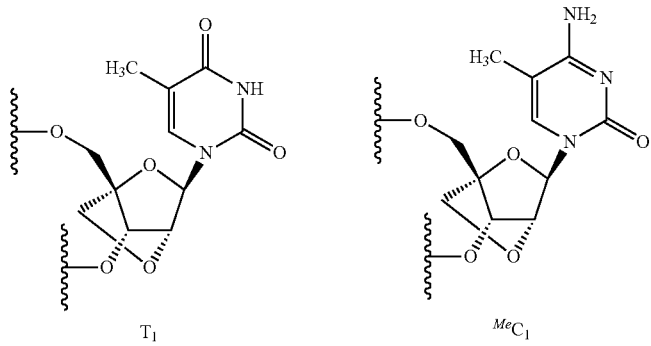

$T_l$        $^{Me}C_l$

| SEQ ID NO./ ISIS NO. | dosage (μmol/kg) | % UTC | ALT (IU/L) | AST (IU/L) |
|---|---|---|---|---|
| 05/392056 | 2.5 | 58 | 38.75 | 70.25 |
|  | 5 | 39 | 319.25 | 62 |
|  | 10 | 18 | 890 | 592.5 |
| 06/403737 | 2.5 | 74 | 26.75 | 41.75 |
|  | 5 | 39 | 132.5 | 102.25 |
|  | 10 | 22 | 481 | 297.5 |
|  | 20 | 11 | 870 | 701 |
| Saline | 0 | 100 | 33.25 | 70.25 |

| SEQ ID NO./ ISIS NO. | Composition (5' to 3') | Wings | ED$_{50}$ (μmol/kg) |
|---|---|---|---|
| 07/392063 | $^{Me}C_lT_l$TAGCACTGGC$^{Me}C_lT_l$ | LNA | 0.67 |
| 08/403736 | $^{Th}C_l{}^{Th}U_l$TAGCACTGGC$^{Th}C_l{}^{Th}U_l$ | 5-thiazole LNA | 0.39 |

All internucleoside linkages are phosphorothioate. Nucleosides not followed by a subscript are β-D-2'-deoxyribonucleosides. Annotated nucleosides are described below.

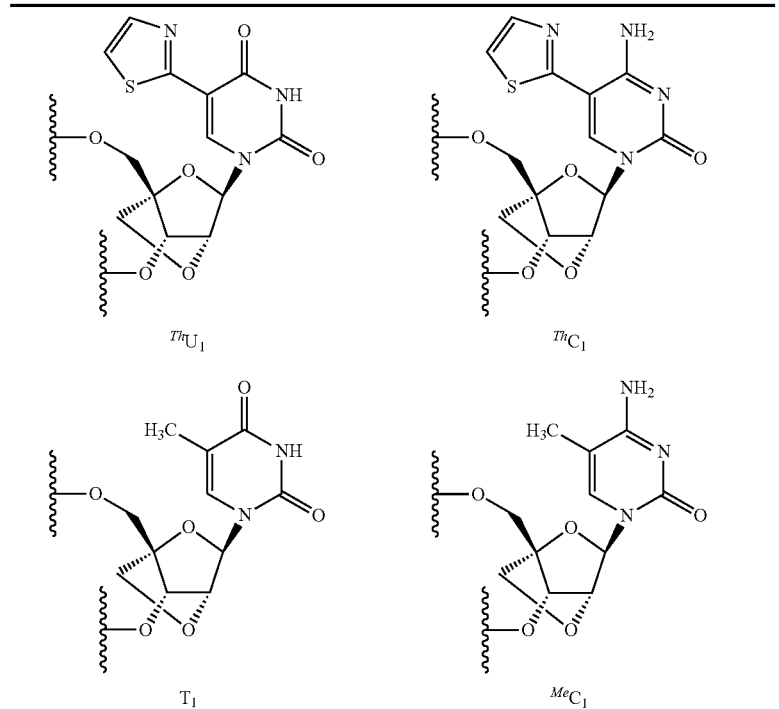

| SEQ ID NO./ ISIS NO. | dosage (μmol/kg) | % UTC | ALT (IU/L) | AST (IU/L) |
|---|---|---|---|---|
| 07/392063 | 0.1 | 98.6 | 26.5 | 48.5 |
| | 0.32 | 75.1 | 32.25 | 48 |
| | 1.0 | 36.1 | 21 | 89 |
| | 3.2 | 6.3 | 128 | 104.75 |
| 08/403736 | 0.1 | 68.3 | 30.25 | 100.25 |
| | 0.32 | 54.8 | 23.25 | 51.75 |
| | 1.0 | 37.4 | 24.75 | 102.5 |
| | 3.2 | 18.3 | 21.5 | 72.25 |
| Saline | 0 | 100 | 31.25 | 106.5 |

The body weights, liver weights, spleen weights and kidney weights were comparable for the different doses of ISIS 392063 and ISIS 403736 with no substantial deviations compared to the saline treated animals.

What is claimed is:

1. A bicyclic nucleoside having Formula I:

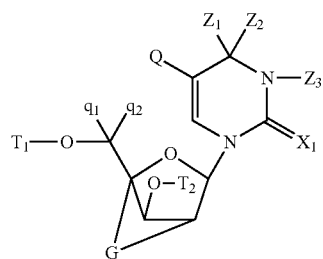

wherein:
one of $T_1$ and $T_2$ is H or a hydroxyl protecting group and the other of $T_1$ and $T_2$ is H, a hydroxyl protecting group or a reactive phosphorus group;

$q_1$ and $q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

$Z_1$ is $NH_2$ or NHPg and $Z_2$ together with $Z_3$ comprise a bond wherein Pg is a protecting group;

or $Z_1$ and $Z_2$ together are $=X_2$ and $Z_3$ is H;

Q is thiazolyl or substituted thiazolyl;

G is a diradical moiety selected from one or more linked groups, wherein each group is independently selected from —C($R_1R_2$)—, —C($R_1$)=C($R_2$)—, —C($R_1$)=N—, —C[=C($R_1R_2$)]—, —C(=O)—, —N($R_1$)—, —N($R_1$)—C(=$X_3$)—, —O—, —S—, —S(=O)— or —S(=O)$_2$— and wherein G forms a 5 or 6 membered ring with the furanose ring of the nucleoside;

$X_1$, $X_2$ and $X_3$ are each, independently, O or S;

$R_1$ and $R_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)$-$N(J_1)(J_2)$ and $C(=L)N(J_1)(J_2)$;

L is O, S or $NJ_3$; and each $J_1$, $J_2$ and $J_3$ is, independently, H, $C_1$-$C_6$ alkyl.

2. The bicyclic nucleoside of claim 1 wherein $q_1$ and $q_2$ are each, independently, H, halogen, $C_1$-$C_6$ alkyl or substituted $C_1$-$C_6$ alkyl.

3. The bicyclic nucleoside of claim 1 wherein $q_1$ and $q_2$ are each H.

4. The bicyclic nucleoside of claim 1 wherein $Z_1$ is $NH_2$ or NHPg and $Z_2$ together with $Z_3$ comprise a bond.

5. The bicyclic nucleoside of claim 1 wherein $Z_1$ and $Z_2$ together are $=X_2$ and $Z_3$ is H.

6. The bicyclic nucleoside of claim 5 wherein $X_2$ is O.

7. The bicyclic nucleoside of claim 1 wherein G is —(C($R_1R_2$))$_n$—, —(C($R_1R_2$))$_n$—O—, —(C($R_1R_2$))$_n$—S—, —(C($R_1R_2$))$_n$—(NR$_1$)—, —C(=O)—N($R_1$)—C($R_1R_2$)—, —C(R$_1$R$_2$)—N(R$_1$)—C(R$_1$R$_2$)—, —C(R$_1$R$_2$)—O—N(R$_1$)—, —C(R$_1$R$_2$)—N(Ri)—O— or —C(R$_1$R$_2$)—C(=C(R$_1$R$_2$))— wherein n is from 1 to 3.

8. The bicyclic nucleoside of claim 1 wherein G is 4'-(CH$_2$)—O-2', 4'-(CH$_2$)$_2$—O-2', 4'-CH(CH$_3$)—O-2', 4'-C(CH$_3$)$_2$—O-2', 4'-CH(CH$_2$OCH$_3$)—O-2', 4'—C(=O)—N(CH$_3$)—CH$_2$-2', 4'-CH$_2$—N(CH$_3$)—CH$_2$-2', 4'-CH$_2$—N(OCH$_3$)-2', 4'-CH$_2$—N(O(CH$_2$)$_2$—OCH$_3$)-2', 4'-CH$_2$—O—N(CH$_3$)-2', 4'-CH$_2$—N(CH$_3$)—O-2', 4'-CH$_2$—CH(CH$_3$)-2' or 4'-CH$_2$—C(=CH$_2$)-2'.

9. The bicyclic nucleoside of claim 1 wherein G is 4'-(CH$_2$)—O-2', 4'-CH(CH$_3$)—O-2', 4'-C(CH$_3$)$_2$—O-2', 4'-CH$_2$—N(OCH$_3$)-2', 4'-CH$_2$—N(O(CH$_2$)$_2$—OCH$_3$)-2', 4'-CH$_2$—O—N(CH$_3$)-2', 4'-CH$_2$—N(CH$_3$)—O-2', 4'-CH$_2$—CH(CH$_3$)-2' or 4'-CH$_2$—C(=CH$_2$)-2'.

10. The bicyclic nucleoside of claim 1 wherein G forms a 5 membered ring with the furanose ring of the nucleoside.

11. The bicyclic nucleoside of claim 1 wherein Q is thiazolyl.

12. The bicyclic nucleoside of claim 1 wherein Q is substituted thiazolyl.

13. The bicyclic nucleoside of claim 1 wherein at least one of T$_1$ and T$_2$ is selected from acetyl, benzyl, t-butyldimethylsilyl, t-butyldiphenylsilyl and dimethoxytrityl.

14. The bicyclic nucleoside of claim 1 wherein T$_1$ is 4,4'-dimethoxytrityl.

15. The bicyclic nucleoside of claim 1 wherein T$_2$ is a reactive phosphorus group selected from diisopropylcyanoethoxy phosphoramidite and H-phosphonate.

16. The bicyclic nucleoside of claim 1 wherein T$_1$ is 4,4'-dimethoxytrityl and T$_2$ is diisopropylcyanoethoxy phosphoramidite.

17. The bicyclic nucleoside of claim 1 having the configuration of Formula II:

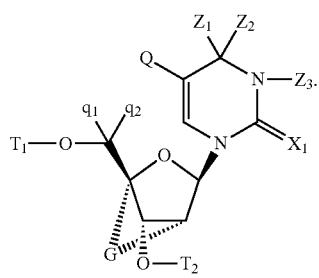

II

18. An oligomeric compound comprising at least one bicyclic nucleoside of Formula III:

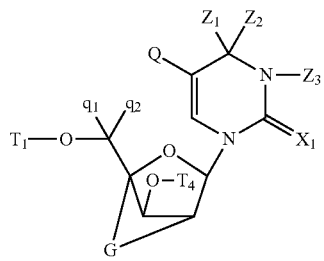

III wherein:
wherein independently for each bicyclic nucleoside of Formula III:

one of T$_3$ and T$_4$ is an internucleoside linking group linking the bicyclic nucleoside to the oligomeric compound and the other of T$_3$ and T$_4$ is H, a hydroxyl protecting group, a 5' or 3'-terminal group or an internucleoside linking group linking the bicyclic nucleoside to the oligomeric compound;

q$_1$ and q$_2$ are each, independently, H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_1$-C$_6$ alkoxyl, substituted C$_1$-C$_6$ alkoxyl, acyl, substituted acyl, C$_1$-C$_6$ aminoalkyl or substituted C$_1$-C$_6$ aminoalkyl;

Z$_1$ is NH$_2$ or NHPg and Z$_2$ together with Z$_3$ comprise a bond wherein Pg is a protecting group;

or Z$_1$ and Z$_2$ together are =X$_2$ and Z$_3$ is H;

Q is thiazolyl or substituted thiazolyl;

G is a diradical moiety selected from one or more linked groups, wherein each group is independently selected from —C(R$_1$R$_2$)—, —C(R$_1$)=C(R$_2$)—, —C(R$_1$)=N—, —C[=C(R$_1$R$_2$)]—, —C(=O)—, —N(R$_1$)—, —N(R$_1$)—C(=X$_3$)—, —O—, —S—, —S(=O)— or —S(=O)$_2$— and wherein G forms a 5 or 6 membered ring with the furanose ring of the nucleoside;

X$_1$, X$_2$ and X$_3$ are each, independently, O or S;

R$_1$ and R$_2$ are each independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_1$-C$_6$ alkoxyl, substituted C$_1$-C$_6$ alkoxyl, acyl, substituted acyl, C$_1$-C$_6$ aminoalkyl or substituted C$_1$-C$_6$ aminoalkyl;

each substituted group comprises one or more optionally protected substituent groups independently selected from halogen, OJ$_1$, N(J$_1$)(J$_2$), =NJ$_1$, SJ$_1$, N$_3$, CN, OC(=L)J$_1$, OC(=L)N(J$_1$)(J$_2$) and C(=L)N(J$_1$)(J$_2$);

L is O, S or NJ$_3$; and each J$_1$, J$_2$ and J$_3$ is, independently, H, C$_1$-C$_6$ alkyl.

19. The oligomeric compound of claim 18 wherein q$_1$ and q$_2$ are each independently, H, halogen, C$_1$-C$_6$ alkyl or substituted C$_1$-C$_6$ alkyl for each bicyclic nucleoside of Formula III.

20. The oligomeric compound of claim 18 wherein q$_1$ and q$_2$ are each H for each bicyclic nucleoside of Formula III.

21. The oligomeric compound of claim 18 wherein Z$_1$ is NH$_2$ or NHPg and Z$_2$ together with Z$_3$ comprise a bond for at least one bicyclic nucleoside of Formula III.

22. The oligomeric compound of claim 18 wherein Z$_1$ and Z$_2$ together are =X$_2$ and Z$_3$ is H for at least one bicyclic nucleoside of Formula III.

23. The oligomeric compound claim 22 wherein each X$_2$ is O.

24. The oligomeric compound of claim 18 wherein G is —(C(R$_1$R$_2$))$_n$—, —(C(R$_1$R$_2$))$_n$—O—, —(C(R$_1$R$_2$))$_n$—S—, —(C(R$_1$R$_2$))$_n$—(NR$_1$)—, —C(=O)—N(R$_1$)—C(R$_1$R$_2$)—, —C(R$_1$R$_2$)—N(Ri)—C(R$_1$R$_2$)—, —C(R$_1$R$_2$)—O—N(Ri)—, —C(R$_1$R$_2$)—N(R$_1$)—O— or —C(R$_1$R$_2$)—C(=C(R$_1$R$_2$))— for each bicyclic nucleoside of Formula III, wherein n is from 1 to 3.

25. The oligomeric compound of claim 18 wherein G is 4'-(CH$_2$)—O-2', 4'-(CH$_2$)$_2$—O-2', 4'-CH(CH$_3$)—O-2', 4'-C(CH$_3$)$_2$—O-2', 4'-CH(CH$_2$OCH$_3$)—O-2', 4'—C(=O)—N(CH$_3$)—CH$_2$-2', 4'-CH$_2$—N(CH$_3$)—CH$_2$-2', 4'-CH$_2$—N(OCH$_3$)-2', 4'-CH$_2$—N(O(CH$_2$)$_2$—OCH$_3$)-2', 4'-CH$_2$—O—N(CH$_3$)-2', 4'-CH$_2$—N(CH$_3$)—O-2', 4'-CH$_2$—CH(CH$_3$)-2' or 4'-CH$_2$—C(=CH$_2$)-2' for each bicyclic nucleoside of Formula III.

26. The oligomeric compound of claim 18 wherein G is 4'-(CH$_2$)—O-2', 4'-CH(CH$_3$)—O-2', 4'-C(CH$_3$)$_2$—O-2', 4'-CH$_2$—N(OCH$_3$)-2', 4'-CH$_2$—N(O(CH$_2$)$_2$—OCH$_3$)-2', 4'-CH$_2$—O—N(CH$_3$)-2', 4'-CH$_2$—N(CH$_3$)—O-2', 4'-CH$_2$—CH(CH$_3$)-2' or 4'-CH$_2$—C(=CH$_2$)-2' for each bicyclic nucleoside of Formula III.

27. The oligomeric compound of claim 18 wherein G forms a 5 membered ring with the furanose ring of the nucleoside for each bicyclic nucleoside of Formula III.

28. The oligomeric compound of claim 18 wherein Q is thiazolyl for each bicyclic nucleoside of Formula III.

29. The oligomeric compound of claim 18 wherein Q is substituted thiazolyl for each bicyclic nucleoside of Formula III.

30. The oligomeric compound of claim 18 wherein at least one of T$_3$ and T$_4$ is a 5' or 3'-terminal group.

31. The oligomeric compound of claim 18 wherein each bicyclic nucleoside of Formula III has the configuration of Formula IV:

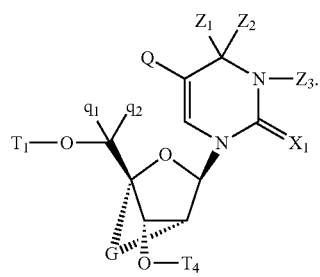

IV

32. The oligomeric compound of claim 18 comprising at least one region of at least two contiguous bicyclic nucleosides having said formula located at either the 3' or the 5'-end of the oligomeric compound.

33. The oligomeric compound of claim 18 comprising a gapped oligomeric compound having two external regions, each external region comprising from 1 to about 5 contiguous bicyclic nucleosides having said formula, wherein one of the external regions is located at the 5'-end and the other of the external regions is located at the 3'-end and wherein the two external regions are separated by an internal region comprising from about 6 to about 14 monomeric subunits independently selected from nucleosides and modified nucleosides.

34. The oligomeric compound of claim 18 comprising from about 8 to about 40 monomers in length.

35. A method of inhibiting the function of a target RNA comprising contacting a cell with an oligomeric compound of claim 18 wherein said oligomeric compound comprises from about 8 to about 40 monomeric subunits and is complementary to said target RNA.

36. The method of claim 35 wherein said cell is in an animal.

37. The method of claim 35 wherein said cell is in a human.

38. The method of claim 35 wherein said target RNA is selected from mRNA, pre-mRNA and micro RNA.

39. The method of claim 35 wherein said target RNA is mRNA.

40. The method of claim 35 wherein said target RNA is human mRNA.

41. The method of claim 35 wherein said target RNA is cleaved thereby inhibiting its function.

42. The method of claim 35 further comprising detecting the levels of target RNA.

* * * * *

SEQUENCE LISTING

<160> NUMBER OF SEQ ID NOS: 8

<210> SEQ ID NO 1
<211> LENGTH: 3160
<212> TYPE: DNA
<213> ORGANISM: H. sapiens

<400> SEQUENCE: 1

```
cctcccctcg cccggcgcgg tcccgtccgc ctctcgctcg cctcccgcct cccctcggtc      60
ttccgaggcg cccgggctcc cggcgcggcg gcggagggggg cggcaggcc ggcgggcggt      120 gatgtggcag gactctttat gcgctgcggc aggatacgcg ctcggcgctg ggacgcgact      180
gcgctcagtt ctctcctctc ggaagctgca gccatgatgg aagtttgaga gttgagccgc      240
tgtgaggcga ggccgggctc aggcgaggga gatgagagac ggcggcggcc gcggcccgga      300
gcccctctca gcgcctgtga gcagccgcgg gggcagcgcc ctcggggagc cggccggcct      360
gcggcggcgg cagcggcggc gtttctcgcc tcctcttcgt cttttctaac cgtgcagcct      420
cttcctcggc ttctcctgaa agggaaggtg gaagccgtgg gctcgggcgg gagccggctg      480
aggcgcggcg gcggcggcgg cggcacctcc cgctcctgga gcgggggggga gaagcggcgg      540 cggcggcggc cgcggcggct gcagctccag ggaggggggtc tgagtcgcct gtcaccattt      600
ccagggctgg gaacgccgga gagttggtct ctcccttct actgcctcca acacggcggc      660
ggcggcggcg gcacatccag ggaccccgggc cggttttaaa cctcccgtcc gccgccgccg      720
caccccccgt ggcccgggct ccggaggccg ccggcggagg cagccgttcg gaggattatt      780
cgtcttctcc ccattccgct gccgccgctg ccaggcctct ggctgctgag gagaagcagg      840
cccagtcgct gcaaccatcc agcagccgcc gcagcagcca ttacccggct gcggtccaga      900
gccaagcggc ggcagagcga ggggcatcag ctaccgccaa gtccagagcc atttccatcc      960
tgcagaagaa gccccgccac cagcagcttc tgccatctct ctcctccttt tcttcagcc      1020 acaggctccc agacatgaca gccatcatca agagatcgt tagcagaaac aaaaggagat      1080
atcaaggaga tggattcgac ttagacttga cctatattta tccaaacatt attgctatgg      1140
gatttcctgc agaaagactt gaaggcgtat acaggaacaa tattgatgat gtagtaaggt      1200
ttttggattc aaagcataaa aaccattaca agatatacaa tctttgtgct gaaagacatt      1260
atgacaccgc caaatttaat tgcagagttg cacaatatcc ttttgaagac cataacccac      1320
cacagctaga acttatcaaa ccctttttgtg aagatcttga ccaatggcta agtgaagatg      1380
acaatcatgt tgcagcaatt cactgtaaag ctggaaaggg acgaactggt gtaatgatat      1440
gtgcatattt attacatcgg ggcaaatttt taaaggcaca agaggcccta gatttctatg      1500
gggaagtaag gaccagagac aaaaagggag taactattcc cagtcagagg cgctatgtgt      1560
attattatag ctacctgtta aagaatcatc tggattatag accagtggca ctgttgtttc      1620
acaagatgat gtttgaaact attccaatgt tcagtggcgg aacttgcaat cctcagtttg      1680
tggtctgcca gctaaaggtg aagatatatt cctccaattc aggacccaca cgacgggaag      1740
acaagttcat gtactttgag ttccctcagc cgttacctgt gtgtggtgat atcaaagtag      1800
agttcttcca caaacagaac aagatgctaa aaaaggacaa aatgtttcac tttgggtaa      1860 atacattctt cataccagga ccagaggaaa cctcagaaaa agtagaaaat ggaagtctat      1920
gtgatcaaga aatcgatagc atttgcagta tagagcgtgc agataatgac aaggaatatc      1980
tagtacttac tttaacaaaa aatgatcttg acaaagcaaa taaagacaaa gccaaccgat      2040
acttttctcc aaattttaag gtgaagctgt acttcacaaa aacagtagag gagccgtcaa      2100
atccagaggc tagcagttca acttctgtaa caccagatgt tagtgacaat gaacctgatc      2160
attatagata ttctgacacc actgactctg atccagagaa tgaacctttt gatgaagatc      2220
agcatacaca aattacaaaa gtctgaattt tttttttatca agagggataa acaccatga      2280 aaataaactt gaataaactg aaaatggacc tttttttttt taatggcaat aggacattgt      2340
gtcagattac cagttatagg aacaattctc ttttcctgac caatcttgtt ttaccctata      2400
```

```
catccacagg gttttgacac ttgttgtcca gttgaaaaaa ggttgtgtag ctgtgtcatg    2460
tatatacctt tttgtgtcaa aaggacattt aaaattcaat taggattaat aaagatggca    2520
ctttcccgtt ttattccagt tttataaaaa gtggagacag actgatgtgt atacgtagga    2580 atttttcct  tttgtgttct gtcaccaact gaagtggcta aagagctttg tgatatactg    2640
gttcacatcc taccccttg  cacttgtggc aacagataag tttgcagttg gctaagagag    2700
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcatttt  ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                          3160

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aatggctaag tgaagatgac aatcat                                         26

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgcacatatc attacaccag ttcgt                                          25

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                     30

<210> SEQ ID NO 5
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 5
tcatggctgc agct                                                      14

<210> SEQ ID NO 6
<211> LENGTH: 14
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 13, 14
<223> OTHER INFORMATION: bases at these positions are RNA

<400> SEQUENCE: 6
ucatggctgc agcu                                                         14

<210> SEQ ID NO 7
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 7
cttagcactg gcct                                                         14

<210> SEQ ID NO 8
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 13, 14
<223> OTHER INFORMATION: bases at these positions are RNA

<400> SEQUENCE: 8
cutagcactg gccu                                                         14
```